(12) United States Patent
Lassalle et al.

(10) Patent No.: US 7,306,797 B2
(45) Date of Patent: Dec. 11, 2007

(54) USE OF A COMPOUND ANTAGONIST OF ESM-1 PROTEIN FOR PRODUCING A MEDICINE FOR TREATING CANCER

(75) Inventors: Philippe Lassalle, Lille (FR); David Bechard, Paris (FR); André-Bernard Tonnel, Premesques (FR)

(73) Assignees: Institut Pasteur de Lille, Lille (FR); Institut National de la Sante et de la Recherche Medicale (Inserm), Paris (FR)

( * ) Notice: Subject to any disclaimer, the term of this patent is extended or adjusted under 35 U.S.C. 154(b) by 110 days.

(21) Appl. No.: 10/416,203

(22) PCT Filed: Nov. 8, 2001

(86) PCT No.: PCT/FR01/03475

§ 371 (c)(1),
(2), (4) Date: Apr. 26, 2004

(87) PCT Pub. No.: WO02/38178

PCT Pub. Date: May 16, 2002

(65) Prior Publication Data

US 2004/0234526 A1  Nov. 25, 2004

(30) Foreign Application Priority Data

Nov. 9, 2000  (FR) .................................. 00 14422

(51) Int. Cl.
*A61K 39/395*  (2006.01)
*A61K 39/00*  (2006.01)

(52) U.S. Cl. ................................ 424/130.1; 424/141.1; 424/277.1

(58) Field of Classification Search ..................... None
See application file for complete search history.

(56) References Cited

U.S. PATENT DOCUMENTS 5,747,280 A * 5/1998 Hastings et al. ........... 435/69.1
6,670,328 B1  12/2003 Lasalle et al.

FOREIGN PATENT DOCUMENTS

FR   2 775 691     5/1998
WO   WO96 17931   6/1996

OTHER PUBLICATIONS

Bechard D, Meignin V, Scherpereel A, Oudin S, Kervoaze G, Bertheau P, Janin A, Tonnel A, Lassalle P. Characterization of the secreted form of endothelial-cell-specific molecule 1 by specific monoclonal antibodies. J Vasc Res. Sep.-Oct 2000;37(5):417-25.*
Bechard et al., J Vasc Res, vol. 37, pp. 417-425, Apr. 2000.*
U.S. Appl. No. 10/416,204, filed May 8, 2003, Lassalle et al.
International Search Report in PCT/FR01/03477.
International Search Report in corresponding PCT/FR01/03475.
Bechard et al.; Characterization of the secreted form of endothelial-cell-specific molecule 1 by specific monoclonal antibodies; J. Vasc. Res. (2000) 37:417-425.
Lassalle et al.; ESM-1 is a novel human endothelial cell-specific molecule expressed in lung and regulated by cytokines; J. Biol. Chem. (1996) vol. 271, No 34 pp. 20458-20464.
Hendrix et al.; Expression of select-endothelial-specific genes by aggressive human melanoma cells: Putative role of VE-Cadherin (CD144) in vasculogenic mimicry; FASEB Journal, vol. 15, No. 5 (2001) p. A743 XP001015835.

* cited by examiner

*Primary Examiner*—Shanon Foley
*Assistant Examiner*—Lei Yao
(74) *Attorney, Agent, or Firm*—Finnegan, Henderson, Farabow, Garrett & Dunner, L.L.P.

(57) ABSTRACT

Use of an antagonist compound of protein ESM-1 for the production of a drug for the treatment of a cancer.

1 Claim, 10 Drawing Sheets

SEQUENCE LISTING

<160> NUMBER OF SEQ ID NOS: 8

<210> SEQ ID NO 1
<211> LENGTH: 184
<212> TYPE: PRT
<213> ORGANISM: Homo sapiens

<400> SEQUENCE: 1

Met Lys Ser Val Leu Leu Leu Thr Thr Leu Leu Val Pro Ala His Leu
 1               5                  10                  15

Val Ala Ala Trp Ser Asn Asn Tyr Ala Val Asp Cys Pro Gln His Cys
            20                  25                  30

Asp Ser Ser Glu Cys Lys Ser Ser Pro Arg Cys Lys Arg Thr Val Leu
        35                  40                  45

Asp Asp Cys Gly Cys Cys Arg Val Cys Ala Ala Gly Arg Gly Glu Thr
    50                  55                  60

Cys Tyr Arg Thr Val Ser Gly Met Asp Gly Met Lys Cys Gly Pro Gly
65                  70                  75                  80

Leu Arg Cys Gln Pro Ser Asn Gly Glu Asp Pro Phe Gly Glu Glu Phe
                85                  90                  95

Gly Ile Cys Lys Asp Cys Pro Tyr Gly Thr Phe Gly Met Asp Cys Arg
            100                 105                 110

Glu Thr Cys Asn Cys Gln Ser Gly Ile Cys Asp Arg Gly Thr Gly Lys
        115                 120                 125

Cys Leu Lys Phe Pro Phe Gln Tyr Ser Val Thr Lys Ser Ser Asn
    130                 135                 140

Arg Phe Val Ser Leu Thr Glu His Asp Met Ala Ser Gly Asp Gly Asn
145                 150                 155                 160

Ile Val Arg Glu Val Val Lys Glu Asn Ala Ala Gly Ser Pro Val
                165                 170                 175

Met Arg Lys Trp Leu Asn Pro Arg
            180

<210> SEQ ID NO 2
<211> LENGTH: 2006
<212> TYPE: DNA
<213> ORGANISM: Homo sapiens

<400> SEQUENCE: 2

```
cttcccacca gcaaagacca cgactggaga gccgagccgg aggcagctgg gaaacatgaa      60
gagcgtcttg ctgctgacca cgctcctcgt gcctgcacac ctggtggccg cctggagcaa     120
taattatgcg gtggactgcc ctcaacactg tgacagcagt gagtgcaaaa gcagcccgcg     180
ctgcaagagg acagtgctcg acgactgtgg ctgctgccga gtgtgcgctg cagggcgggg     240
agaaacttgc taccgcacag tctcaggcat ggatggcatg aagtgtggcc cggggctgag     300
gtgtcagcct tctaatgggg aggatccttt tggtgaagag tttggtatct gcaaagactg     360
tccctacggc accttcggga tggattgcag agagacctgc aactgccagt caggcatctg     420
tgacagggg acgggaaaat gcctgaaatt ccccttcttc aatattcag taaccaagtc     480
ttccaacaga tttgtttctc tcacggagca tgacatggca tctggagatg caatattgt     540
gagagaagaa gttgtgaaag agaatgctgc cgggtctccc gtaatgagga aatggttaaa     600
tccacgctga tcccggctgt gatttctgag agaaggctct attttcgtga ttgttcaaca     660
cacagccaac attttaggaa ctttctagat atagcataag tacatgtaat ttttgaagat     720
ccaaattgtg atgcatggtg atccagaaa acaaaaagta ggatacttac aatccataac     780
atccatatga ctgaacactt gtatgtgttt gttaaatatt cgaatgcatg tagatttgtt     840
aaatgtgtgt gtatagtaac actgaagaac taaaaatgca atttaggtaa tcttacatgg     900
agacaggtca accaaagagg gagctaggca aagctgaaga ccgcagtgag tcaaattagt     960
tctttgactt tgatgtacat taatgttggg atatggaatg aagacttaag agcaggagaa    1020
gatgggagg gggtgggagt gggaaataaa atatttagcc cttccttggt aggtagcttc    1080
tctagaattt aattgtgctt tttttttttt tttggctttg ggaaaagtca aaataaaaca    1140
accagaaaac ccctgaagga agtaagatgt ttgaagctta tggaaatttg agtaacaaac    1200
agctttgaac tgagagcaat ttcaaaaggc tgctgatgta gttcccgggt tacctgtatc    1260
tgaaggacgg ttctggggca taggaaacac atacacttcc ataaatagct ttaacgtatg    1320
ccacctcaga gataaatcta agaagtattt tacccactgg tggtttgtgt gtgtatgaag    1380
gtaaatattt atatattttt ataaataaat gtgttagtgc aagtcatctt ccctacccat    1440
atttatcatc ctcttgagga aagaaatcta gtattatttg ttgaaaatgg ttagaataaa    1500
aacctatgac tctataaggt tttcaaacat ctgaggcatg ataaatttat tatccataat    1560
tataggagtc actctggatt tcaaaaaatg tcaaaaaatg agcaacagag ggaccttatt    1620
taaacataag tgctgtgact tcggtgaatt ttcaatttaa ggtatgaaaa taagttttta    1680
ggaggtttgt aaaagaagaa tcaattttca gcagaaaaca tgtcaacttt aaaatatagg    1740
tggaattagg agtatatttg aaagaatctt agcacaaaca ggactgttgt actagatgtt    1800
cttaggaaat atctcagaag tatttttattt gaagtgaaga acttatttaa gaattatttc    1860
agtatttacc tgtatttat tcttgaagtt ggccaacaga gttgtgaatg tgtgtggaag    1920
gcctttgaat gtaaagctgc ataagctgtt aggttttgtt ttaaaaggac atgttttatta    1980
ttgttcaata aaaagaaca agatac                                        2006
```

<210> SEQ ID NO 3

-continued

```
<211> LENGTH: 30
<212> TYPE: DNA
<213> ORGANISM: Artificial Sequence
<220> FEATURE:
<223> OTHER INFORMATION: Description of Artificial Sequence: Primer

<400> SEQUENCE: 3
gcctgaaatt ccccgccttc caatattcag                              30

<210> SEQ ID NO 4
<211> LENGTH: 30
<212> TYPE: DNA
<213> ORGANISM: Artificial Sequence
<220> FEATURE:
<223> OTHER INFORMATION: Description of Artificial Sequence: Primer

<400> SEQUENCE: 4
ctgaatattg gaaggcgggg aatttcaggc                              30

<210> SEQ ID NO 5
<211> LENGTH: 34
<212> TYPE: DNA
<213> ORGANISM: Artificial Sequence
<220> FEATURE:
<223> OTHER INFORMATION: Description of Artificial Sequence: Primer

<400> SEQUENCE: 5
cctgaaattc cccttcgccc aatattcagt aacc                         34

<210> SEQ ID NO 6
<211> LENGTH: 34
<212> TYPE: DNA
<213> ORGANISM: Artificial Sequence
<220> FEATURE:
<223> OTHER INFORMATION: Description of Artificial Sequence: Primer

<400> SEQUENCE: 6
ggttactgaa tattgggcga agggaatttt cagg                         34

<210> SEQ ID NO 7
<211> LENGTH: 34
<212> TYPE: DNA
<213> ORGANISM: Artificial Sequence
<220> FEATURE:
<223> OTHER INFORMATION: Description of Artificial Sequence: Primer

<400> SEQUENCE: 7
cctgaaattc cccgccgccc aatattcagt aacc                         34

<210> SEQ ID NO 8
<211> LENGTH: 34
<212> TYPE: DNA
<213> ORGANISM: Artificial Sequence
<220> FEATURE:
<223> OTHER INFORMATION: Description of Artificial Sequence: Primer

<400> SEQUENCE: 8
ggttactgaa tattgggcgg cggggaattt cagg                         34
```

USE OF A COMPOUND ANTAGONIST OF ESM-1 PROTEIN FOR PRODUCING A MEDICINE FOR TREATING CANCER

SCOPE OF THE INVENTION

The present invention relates to the fields of prevention and/or treatment of cancers.

STATE OF THE ART

Despite huge financial and human investments, cancer remains one of the major causes of death.

Cancer is frequently a disease associated with defects in the system of intracellular signaling. Normal cells respond to numerous extracellular signals by proliferating, differentiating or more generally changing their metabolic activity. Such signals are received on the surface of the cells and converted by a system of signal transduction proteins into a message recognized by the cell. This message is responsible for subsequent cell regulation phenomena.

Metastasis is the formation of a secondary tumour colony at a site distant from the initial tumour. It represents a multi-step process for which the tumoral invasion is an early event. The tumour cells escape locally across the barrier tissues, such as the basal membrane of the epithelium, and reach the interstitial stroma, from which they gain access to the blood vessels or the lymph canals before subsequent dissemination. After having invaded the endothelial layer of the vascular wall, the circulating tumour cells are carried around by the blood circulation and are stopped in the precapillary venules of the target organ by adhesion to the lumen surfaces of the endothelial cell, or are exposed to the basal membranes. The tumour cells leave the vascular wall and enter into the parenchyma of the organ. Finally, the tumour cell, after extravasation, multiplies in a different tissue from that in which it originated.

It has been shown that some cancers are caused by defects associated with genes responsible for the transduction of the signal. Such genes are called oncogenes. These oncogenes may lead to an overexpression of one or more signal transduction proteins inducing an abnormal cell proliferation. The defective signals may be linked to various mechanisms.

Some anticancer therapies aim to inhibit the expression or the bioavailability of the oncogenic proteins responsible for the proliferation of the cancer cells, such as the proteins of the MAP kinase family or the products of certain oncogenes such as c-myc.

Protein ESM-1 is a polypeptide of 184 amino acids secreted by the endothelial cells and which was described for the first time by LASSALLE et al. (1996). The messenger RNAs coding for protein ESM-1 are mainly found in the endothelial cells and in pulmonary and renal tissues. The expression of the gene coding for ESM-1 is regulated by the cytokines. TNF-α and L'IL-1β induce an increase in the expression of the ESM-1 gene in the endothelial cells of the human umbilical vein, while γ-Interferon reduces its expression.

A high level of circulating protein ESM-1 has been found in patients presenting a systemic inflammatory syndrome, such as septic shock (BECHARD et al., 2000).

Current hospital treatment for cancer predominantly makes use of radiation and/or chemotherapeutic agents, such as vinblastine or adriamycine. However, the widely known undesirable effects of such treatments render these strategies very difficult for the patient to support.

The object of the present invention is to supply anti-cancer compounds which overcome the disadvantages of the methods of therapeutic treatment of cancer in the state of the art.

SUMMARY OF THE INVENTION

A first object of the invention consists of the use of an antagonist compound of protein ESM-1 for the production of a drug for the treatment of a cancer.

According to a first embodiment, an antagonist compound of the invention is an antibody specifically binding to protein ESM-1.

According to a second embodiment, an antagonist compound used in the scope of the invention is a peptide of at least 10 amino acids of a modified protein ESM-1 and which contains the amino acid grouping Ala(134)-Ala(135).

According to a third embodiment, an antagonist compound of protein ESM-1 consists of an antisense oligonucleotide hybridizing with the cDNA coding for ESM-1.

A further object of the invention consists of an antagonist compound of protein ESM-1, chosen from among the antagonist compounds defined above.

The invention also relates to a pharmaceutical composition intended for the treatment of cancer comprising an antagonist compound of protein ESM-1.

Another object of the invention consists of a method for preventing cancer comprising a step in which an antagonist compound of protein ESM-1 is administered.

The invention also concerns a method for the therapeutic treatment of cancer comprising a step in which an antagonist compound of protein ESM-1 is administered.

DETAILED DESCRIPTION OF THE INVENTION

It has been shown for the first time according to the invention that protein ESM-1 is secreted in humans in the form of a proteoglycan of the chondroitin/dermatan sulfate type and that the secreted protein ESM-1 is able to stimulate in vitro the mitogenic activity of the factor HGF/SF (Hepatocyte growth factor/scatter factor).

HGF/SF is an important factor in the appearance of renal multicystic dysplasias and in the appearance of hyperproliferation of the renal tubules and has also been associated with the development of carcinomas of the breast, kidneys and lungs and also the development of malignant melanomas.

It has also been shown according to the invention that transfected human renal epithelial cells expressing protein ESM-1 have a strong tumoral potential and cause the appearance of a renal carcinoma in vivo in mice. It has also been shown that antibodies directed against protein ESM-1 were able to inhibit the development of a renal tumour in vivo and that a peptide antagonist of protein ESM-1 had the same anti-tumoral activity.

In addition, an increase of the serum level of protein ESM-1 in patients with a broncho-pulmonary carcinoma has been shown according to the invention In consequence, a first object of the invention consists of the use of an antagonist compound of protein ESM-1 for the production of a drug for the prevention and/or treatment of cancer.

GENERAL DEFINITIONS

The expressions "protein ESM-1" or "polypeptide of ESM-1", in the context of the invention, include a polypeptide of 184 amino acids referenced as sequence SEQ ID N°1 in the list of sequences, and also a polypeptide of 165 amino acids identical to the polypeptide of sequence SEQ ID N°1 in which the 19 amino acids of the N-terminal end corresponding to the signal peptides are absent, this polypeptide of 165 amino acids comprising the secreted form of the polypeptide of sequence SEQ ID N°1. Also included in the definition of "protein ESM-1" and "polypeptide of ESM-1" respectively are a glycopeptide of 184 amino acids of sequence SEQ ID N°1 and a polypeptide of 165 amino acids corresponding to the sequence running from the amino acid in position 20 to the amino acid in position 184 of the sequence SEQ ID N°1 whose serine residue in position 137 has been modified by O-glycosylation, the O-glycosylated forms of the protein ESM-1 being also designated "glycopeptides" in the present description. The ESM-1 glycopeptide preferably has the serine residue in position 137 which is O-glycosylated by a chondroitin/dermatan sulfate group.

By "antagonist compound" of protein ESM-1, should be understood according to the invention a compound able significantly to reduce the bioavailability of protein ESM-1 compared to target molecules onto which protein ESM-1 naturally fixes. An antagonist compound of protein ESM-1 may reduce the bioavailability of these proteins by reducing the probability of the binding of protein ESM-1 to the target molecules of the organism onto which it naturally fixes. An antagonist compound according to the invention may reduce the bioavailability of protein ESM-1 by inhibiting or blocking the transcription of the gene coding for ESM-1, by inhibiting or blocking the translation of the corresponding messenger RNA, by modifying the intracellular maturation of protein ESM-1, for example by affecting the enzymatic process leading to its glycosylation, or by inhibiting or blocking the secretion of the mature protein ESM-1.

A first object of the invention consists of the use of an antagonist compound of protein ESM-1 for the production of a drug for the treatment of a cancer.

An antagonist compound of protein ESM-1 may be of any type, polypeptide, saccharide, or any organic or inorganic compound causing the reduction of the bioavailability of protein ESM-1 compared to the target molecules onto which this protein fixes.

Antagonist Compounds of Protein ESM-1 of the Antibody Type

A first family of preferred antagonist compounds of ESM-1 according to the invention is composed of antibodies specifically binding to protein ESM-1.

It has been shown according to the invention that antibodies directed specifically against protein ESM-1 are able to inhibit or block the tumorigenic power of this protein. Anti-ESM-1 antibodies thus constitute antagonist compounds of major therapeutic value.

By "antibody" in the context of the invention, should be understood in particular polyclonal or monoclonal antibodies or their fragments (for example the fragments Fab or F(ab)'$_2$) or any polypeptide containing a domain of the initial antibody recognizing protein ESM-1.

Monoclonal antibodies may be prepared from a hybridoma according to the technique described by KOHLER and MIELSTEIN (1975).

They may also be antibodies directed against ESM-1 or a fragment of this protein produced by the trioma technique or the hybridoma technique described by KOZBOR et al. (1983).

They may also be single chain Fv antibody fragments (ScFv) such as those disclosed in the U.S. Pat. No. 4,9476,778 or by MARTINEAU et al. (1998).

Anti-ESM-1 antibodies according to the invention also comprise fragments of antibodies obtained using phage banks such as described by RIDDER et al. (1995) or human antibodies such as described by REINMANN et al. (1997) or by LEGER O J, et al., 1997.

They may also be anti-ESM-1 antibodies produced according to the techniques described by BECHARD et al. (2000). The antibodies described by BECHARD et al. (2000) are monoclonal antibodies secreted by hybrdoma lines prepared from mouse spleen cells previously immunized against the C-terminal fragment of molecular weight 14 kD of ESM-1 which has been produced in *Escherichia coli*, in other words a nonglycosylated fragment of protein ESM-1. By epitope mapping, BECHARD et al. (2000) were able to classify the monoclonal antibodies produced by different hybridoma lines according to the region of protein ESM-1 recognized by them.

A first preferred family of antibodies according to the invention which comprises antagonist compounds of protein ESM-1 are the monoclonal antibodies specifically recognizing the region running from the proline residue in position 79 up to the cysteine residue in position 99 of sequence SEQ ID N°1, this region representing the antigenic determinant D1. They are preferably monoclonal antibodies produced by the hybridoma line deposited at the Collection Nationale de Cultures de Microorganismes of the Institut Pasteur (CNCM) under the access number N°I-1944, also named antibody MEP21.

Other preferred monoclonal antibodies are those specifically binding to the part of protein ESM-1 contained between the glycine residue in position 159 and the arginine residue in position 184 of sequence SEQ ID N°1 which is the region comprising the antigenic determinant D3. Specific preferred monoclonal antibodies of the antigenic determinant D3 may be obtained from the hybridoma line I-1943 (MEP19), deposited on 19 Nov. 1997 at the Collection Nationale de Cultures des Micro-organismes of the Institut Pasteur (CNCM).

Other preferred monoclonal antibodies according to the invention are the monoclonal antibodies specifically binding to the region contained between the serine residue in position 119 and the valine residue in position 139 of protein ESM-1 of sequence SEQ ID NO:1, this region being defined as the antigenic determinant D2 of protein ESM-1. Preferred monoclonal antibodies specifically binding to antigenic determinant D2 of ESM-1 may be obtained from the hybridoma line MEP08 deposited on 19 Nov. 1997 at the Collection Nationale de Cultures de Micro-organismes of the Institut Pasteur (CNCM), at 28 Rue du Docteur Roux, F-75724,Paris, Cedex 15 under Accession No. I-1941.

Other monoclonal antibodies of interest constituting antagonist compounds of protein ESM-1, within the scope of the invention, are the monoclonal antibodies specifically directed against the N-terminal part of protein ESM-1. The preferred monoclonal antibodies directed against the N-terminal part of protein ESM-1 may be obtained from the hybridoma line MEC15 deposited at the Collection Nationale de Cultures des Micro-organismes of the INSTITUT PASTEUR (CNCM) on 17 Oct. 2000 under the access number I-2572.

According to a preferred embodiment, the anti-ESM1 antibodies having the best antagonist activities against ESM-1 are chosen from among the antibodies specifically recognizing the epitopes localized in the region around the phenylalanine residue in position 115. They are in particular the antibodies specifically binding to the region contained between the serine residue in position 119 and the valine residue in position 139 of protein ESM-1 of sequence SEQ ID N°1, such as the monoclonal antibody MEP08 described above.

It has been shown according to the invention that the monoclonal antibody MEP08 is able to inhibit the pro-tumoral activity of protein ESM-1 on the formation of tumours caused by the proliferation of human cells of renal origin in mice.

Polypeptide Antagonists of Protein ESM-1

It has been shown according to the invention that the region containing the antigenic determinant D2 of protein ESM-1 is important for the pro-tumoral activity of protein ESM-1.

In particular, the applicant has synthesized a polypeptide derived from protein ESM-1 in which the phenylalanine residues in positions 134 and 135 of sequence SEQ ID N°1, in other words the residues in positions 115 and 116 of the secreted protein ESM-1, have been replaced by two alanine residues. The applicant has shown that this modified polypeptide was not able to induce tumours in mice. Such a modified polypeptide could thus compete with protein ESM-1, produced at a high level in cancer patients, for its potentializing action with growth factors such as HGF/SF or growth factors FGF-2 and FGF-7.

The antagonist compounds of protein ESM-1 include polypeptides with a length of at least 10 consecutive amino acids of sequence SEQ ID N°1, which includes a sequence of amino acids running from the amino acid in position 119 up to the amino acid in position 139 of sequence SEQ ID N°1, such an antagonist polypeptide of ESM-1 containing at least one substitution of an amino acid, compared to the sequence corresponding to protein ESM-1.

An antagonist polypeptide of protein ESM-1 such as defined above preferably has at the most 11, 12, 13, 14, 15, 16, 17, 18, 19, 20, 21, 22, 23, 24, 25, 30, 35, 40, 45 or 50 consecutive amino acids of sequence SEQ ID N°1 and at least one substitution of amino acids, compared to sequence SEQ ID n°1.

An antagonist polypeptide of protein ESM-1, such as defined above, contains at the most 1, 2, 3, 4, 5, 6, 7, 8, 9 or 10 substitutions of an amino acid, compared to the sequence SEQ ID N°1, the number of substitutions of amino acids being adapted as a function of the length of the polypeptide, it being understood that the number of substitutions of amino acids compared to the sequence SEQ ID N°1 in an antagonist polypeptide according to the invention is at the most 25% of the amino acids contained in the sequence of this antagonist polypeptide, preferably at most 20%, 15% and more preferably at most 10% of the number of amino acids contained in the sequence of the antagonist polypeptide of ESM-1.

A substitution of amino acids, compared to the sequence SEQ ID N°1, in an antagonist polypeptide according to the invention is preferably a "non-conservative" substitution. By "non-conservative" substitution should be understood the substitution of an amino acid residue by an amino acid of a different class.

Amino acids are conventionally classified according to the following classes:

non polar amino acids (hydrophobic): alanine, leucine, isoleucine, valine, proline, phenylalanine, tryptophan and methionine;

amino acids containing aromatic rings: phenylalanine, tryptophan and tyrosine;

neutral polar amino acids: glycine, serine, threonine, cysteine, tyrosine, asparagine and glutamine;

positively charged amino acids (basic): arginine, lysine and histidine);

negatively charged amino acids (acid): aspartic acid and glutamic acid.

A preferred type of substitution of amino acids for the preparation of an antagonist polypeptide of protein ESM-1 according to the invention is the substitution of an amino acid containing an aromatic ring by an amino acid not containing an aromatic ring.

An antagonist polypeptide of protein ESM-1 according to the invention preferably contains a substitution of the phenylalanine residues in positions 134 and 135 of SEQ ID N°1 by two amino acid residues, identical or different, not containing an aromatic ring.

Such a preferred antagonist polypeptide of protein ESM-1 is a polypeptide of at least 10 consecutive amino acids of sequence SEQ ID N°1, such as defined above, in which the phenylalanine residues in positions 134 and 135 have been replaced by two alanine residues.

According to a first embodiment, an antagonist polypeptide of protein ESM-1 according to the invention may be prepared by conventional chemical synthesis techniques, either in homogenous solution or in the solid phase.

As an illustration, an antagonist polypeptide of protein ESM-1 may be prepared by the homogeneous solution technique described by HOUBEN WEIL (1974) or by the solid phase synthesis technique described by MERRIFIELD (1965a; 1965b) and MERRIFIELD 1965b.

An antagonist polypeptide of protein ESM-1 according to the invention may also be prepared by genetic recombination.

In order to produce an antagonist polypeptide of protein ESM-1 such as defined above, a method may be used comprising the steps of:

a) inserting a nucleic acid coding for the antagonist polypeptide of protein ESM-1 in an appropriate expression vector;

b) culturing, in an appropriate culture medium, a host cell previously transformed or transfected with the recombinant expression vector of step a);

c) recovering the culture medium or lysing the host cell, for example by sonication or osmotic shock;

d) separating and purifying from said culture medium or cell lysates obtained in step c), said antagonist polypeptide;

e) if appropriate, characterizing the recombinant antagonist polypeptide thus produced.

The antagonist polypeptides according to the invention may be characterized by fixation on an immunoaffinity chromatography column on which the antibodies directed against this polypeptide or against a fragment of it have previously been immobilized.

According to another embodiment, an antagonist polypeptide of ESM-1 may be purified by passage over an appropriate series of chromatography columns, according to methods known to a person skilled in the art and described for example by AUSUBEL F. et al. (1989).

Antagonist Compounds of Protein ESM-1 of the Antisense Oligonucleotide Type.

Another preferred family of antagonist compounds of protein ESM-1 aiming to reduce the bioavailability of protein ESM-1 secreted in patients at risk or in patients having already developed tumours are compounds able to inhibit or block the expression of the gene coding for ESM-1 in humans.

Such antagonist compounds of protein ESM-1 may be antisense polynucleotides.

The antagonist compounds of protein ESM-1 according to the invention thus include an antisense polynucleotide able to hybridize specifically to a given region of the gene coding for protein ESM-1 and able to inhibit or to block its transcription and/or its translation.

The sequence of the human ESM-1 gene is referenced under the access number AJ401 1091 and AJ401 1092 in the database Genbank.

An antisense polynucleotide according to the invention preferably contains a sequence complementary to a sequence localized in the region of the 5'-end of the DNA of the ESM-1 gene, and more preferably close to the initiation codon of the translation (ATG) of the ESM-1 gene.

According to a second preferred embodiment, an antisense polynucleotide according to the invention contains a sequence complementary to one of the sequences localized at the exon/intron junctions of the ESM-1 gene and preferably sequences corresponding to a splicing site.

A preferred antisense polynucleotide according to the invention contains at least 15 consecutive nucleotides of the cDNA coding for ESM-1 having the nucleotide sequence SEQ ID N°2.

For the purposes of the present invention, a first polynucleotide is considered as being "complementary" to a second polynucleotide when each base of the first nucleotide is paired with the complementary base of the second polynucleotide whose direction is inversed. The complementary bases are A and T (or A and U), and C and G.

In general, an antisense polynucleotide according to the invention has at least 20, 25, 30, 35, 40, 50, 75, 100, 150, 200, 300, 400, 500, 1000 or 2000 consecutive nucleotides of the cDNA of ESM-1 of sequence SEQ ID N°2.

As an illustration, a preferred antisense polynucleotide according to the invention consists of a nucleic acid of complementary sequence to the nucleic acid of the cDNA of ESM-1 of sequence SEQ ID N°2.

An antisense polynucleotide comprising an antagonist compound of protein ESM-1 according to the invention may be prepared by any suitable method well known to a person skilled in the art, including cloning and the action of a restriction enzyme or by chemical synthesis according to techniques such as the phosphodiester method of NARANG et al. (1979) or of BROWN et al. (1979), the diethylphosphoramidite method of BEAUCAGE et al. (1980) or the solid support technique disclosed in the European patent n°EP-0 707 592.

In general, antisense polynucleotides must have a length and a melting point sufficient to allow the formation of an intracellular duplex hybrid having sufficient stability to inhibit the expression of the mRNA of ESM-1. Strategies to construct antisense polynucleotides are in particular described by GREEN et al. (1986) and IZANT and WEINTRAUB (1984).

Methods for construction of antisense polynucleotides are also described by ROSSI and al (1991) and in the PCT applications N°WO 947/23.026, WO 95/04141, WO 92/L18.522 and in the European patent application n° EP 0 572 287.

Other methods for the use of antisense polynucleotides are for example those described by SCZAKIEL et al. (1995) or those disclosed in the PCT application N°WO 95/24,223.

A skilled person may advantageously refer to the methods of production and use of antisense polynucleotides inhibiting or blocking the expression of genes associated with the development of cancers, such as the techniques disclosed in the U.S. Pat. No. 5,582,986 which discloses antisense oligonucleotides for inhibiting the ras gene, the technique described by HOLT et al. (1988) which describes antisense oligonucleotides specifically hybridizing with messenger RNAs of the oncogene c-myb or the technique described by WICKSTRON et al. (1988) which describes antisense oligonucleotides specifically hybridizing with the messenger RNA of the gene c-myc.

Other techniques for using antisense polynucleotides usable by a skilled person are those of SALE et al. (1995) and that of GAO et al. (1996).

Method for Selecting an Antagonist Compound of Protein ESM-1

An antagonist compound of protein ESM-1 according to the invention may be selected by a person skilled in the art for its capacity to inhibit the development of a tumour induced by protein ESM-1 in vivo.

According to a first embodiment, a method for selecting an antagonist compound of protein ESM-1 comprises the following steps:

a) injecting an animal with cells able to form tumours in the presence of protein ESM-1, said cells being transfected or transformed by a nucleic acid able to express protein ESM-1 in vivo;

b) administering to this animal a candidate antagonist compound of protein ESM-1;

c) comparing the formation of tumours in a first animal such as obtained after step b) and in a second animal such as obtained after step a); and d) selecting the candidate compound able to inhibit or block the formation of tumours in the first animal.

The animal used in the selection method above is preferably a non-human mammal, advantageously a rodent, and more preferably a rat, guinea pig or mouse.

In a particular embodiment of the method, this includes a step e) consisting of sacrificing the first and the second animal.

Advantageously, the cell line able to form tumours in the animal in the presence of protein ESM-1 is the line HEK 293 (ATCC N°CRL 1573).

According to a further embodiment, an antagonist compound of protein ESM-1 according to the invention may be selected according to a method using the demonstration of the fixation of a candidate compound onto protein ESM-1. Such a method of selection of a candidate antagonist compound of protein ESM-1 comprises the following steps:

a) supplying a polypeptide consisting of protein ESM-1 or a peptide fragment of this protein;

b) placing said polypeptide in contact with the candidate compound to be tested;

c) detecting the complexes formed between said polypeptide and the candidate compound;

d) selecting the candidate compounds fixing onto the polypeptide consisting of protein ESM-1 or a peptide fragment of this protein.

By "fragment" of protein ESM-1, should be understood a polypeptide containing at least 20, preferably at least 30, 35, 40, 50, 55, 60, 65, 70, 75, 80, 85, 90, 95, 100, 110, 120, 130, 140 or 150 consecutive amino acids of the polypeptide ESM-1 of sequence SEQ ID N°1 and containing the sequence running from the proline residue in position 133 up to the valine residue in position 138 of SEQ ID N°1.

The invention also relates to a kit for selecting a candidate antagonist compound of protein ESM-1, this kit comprising:

a) a purified preparation of a polypeptide consisting of protein ESM-1 or of a fragment of this protein;

b) where appropriate, means of detection of a complex formed between the polypeptide and the candidate compound to be tested.

The method of detection of a complex formed between the polypeptide derived from protein ESM-1 and the candidate compound may be performed by various techniques, such as microdialysis coupled with an HPLC method as described by WANG et al. (1997) or affinity capillary electrophoresis as described by BOUSH et al. (1997).

A candidate compound may be of any type, and particularly the final product of a combinatorial chemistry method.

A. Candidate Compounds Obtained from Peptides Banks

A candidate antagonist compound of protein ESM-1 may be selected according to the method above as an expression product of a DNA insert contained in a phage vector according to the technique described by PARMLEY & SMITH (1988). In this type of peptide bank, the DNA inserts code for peptides of 8 to 20 amino acids in length, as is described by OLDENBURG K R et al. (1992), VALADON P et al. (1996), LUCAS A H (1994), WESTERINK (1995), FELICI et al. (1991).

According to this particular embodiment, the recombinant phages expressing a protein able to fix onto the polypeptide consisting of protein ESM-1 or a fragment of it are retained and the complex formed between protein ESM-1 or a fragment of it and the recombinant phage may be subsequently immunoprecipitated by an anti-ESM-1 monoclonal or polyclonal antibody.

B. Candidate Compound Obtained by Competition Experiments

The candidate antagonist compounds of protein ESM-1 may also be selected by the fact that they fix onto protein ESM-1, or onto a polypeptide fragment of it, in competition with a previously selected antagonist compound of protein ESM-1 such as one of the anti-ESM-1 antibodies described above, and particularly the monoclonal antibody secreted by the hybridoma line MEPOB deposited on 19 Nov. 1997 at the CNCM under the access number 1-1941.

Such competition experiments are for example described in the article by BECHARD et al. (2000).

C. Candidate Antagonist Compounds of Protein ESM-1 Selected by Affinity Chromatography.

Proteins or other molecules of any type able to fix onto protein ESM-1, or to a polypeptide fragment of this protein, may be selected by using affinity columns on which protein ESM-1 or a fragment of it have previously been immobilized, for example by conventional techniques, including the chemical coupling of protein ESM-1 or a fragment of it with the matrix of a column such as of agarose, or AffiGel®. A solution containing the candidate compound to be tested is placed in contact with the chromatographic support on which protein ESM-1 or a peptide fragment of it has been immobilized. The compounds retained on the affinity column are positively selected.

D. Candidate Compounds Selected by Optical Biocaptor Techniques

A candidate antagonist compound of protein ESM-1 may also be selected by using an optical biocaptor such as described by EDWARDS and LEATHERBARROW (1997). This technique allows the detection of interactions between molecules in real time without the necessity of using marked molecules. This technique is based on SPR (Surface Plasmon Resonance). Briefly, the candidate compound to be tested is fixed onto a surface, such as a carboxymethyidextran matrix. A light ray is directed onto the part of the surface which does not contain the sample to be tested and is reflected by this surface. The SPR phenomenon causes a reduction in the intensity of the reflected light with a specific association between the angle of the reflected light and the wavelength of the light ray. The fixation of the candidate compound causes a change in the refractive index of the surface, the change in the refractive index being detected as a modification of the SPR signal.

Such a detection method by optical biocaptor may also permit the selection of candidate compounds which enter into competition with another ligand for the fixation onto protein ESM-1 or a peptide fragment of it.

For example, a candidate antagonist compound of protein ESM-1 includes compounds able to inhibit the fixation of an anti-ESM-1 antibody onto protein ESM-1, to inhibit the fixation of factor HGF-SF or factors FGF-2 and FGF-7 onto protein ESM-1 or a peptide fragment of this protein.

Thus, according to a further embodiment, the invention relates to a method of selection of an antagonist compound of protein ESM-1 characterized in that it comprises the following steps:

a) Placing protein ESM-1 or a peptide fragment of it in contact with:

(i) an antagonist compound of protein ESM-1 fixing onto protein ESM-1; and (ii) a candidate compound to be tested;

b) in a separate step from step a), but optionally simultaneously with it, placing protein ESM-1 or a peptide fragment of it in contact with an antagonist compound of protein ESM-1 fixing onto protein ESM-1;

c) detecting the respective quantity of antagonist compound of protein ESM-1 fixed after each of steps a) and b); and d) selecting the candidate compound which enters into competition with the antagonist compound for the fixation onto protein ESM-1.

An antagonist compound of ESM-1 for the use of the selection method above is preferably an anti-ESM-1 antibody or a peptide antagonist compound such as defined above in the present description.

In a first embodiment of a method for selecting an antagonist compound of ESM-1 from a candidate compound, said method comprises the following steps:

1) selecting, among the candidate compounds, the compounds which fix onto protein ESM-1 or onto a peptide fragment of this protein;

2) administering a compound selected in step 1) to an animal and determining the capacity of this compound to inhibit, in this animal, the development of tumours induced by protein ESM-1;

3) selecting the compounds which inhibit the development of tumours determined in step 2) as antagonist compounds of protein ESM-1.

Step 1) preferably consists of the use of a selection method of a candidate compound fixing onto protein ESM-1 or onto a peptide fragment of this protein, chosen from among the methods detailed in the present description.

Step 2) preferably consists of the use of a selection method of a candidate compound in vivo such as is detailed in the description.

In a particular embodiment of the method, this also contains a step 4) consisting of sacrificing the animal.

Pharmaceutical Composition of the Invention.

A further object of the invention is a pharmaceutical composition for the treatment and/or prevention of a cancer containing an antagonist compound of protein ESM-1.

Pharmaceutical Composition Containing an Antagonist Compound of the Antibody Type or of the Peptide Type According to the Invention.

According to a first embodiment, a pharmaceutical composition according to the invention contains a therapeutically effective quantity of an anti-ESM-1 antibody or of a peptide antagonist compound derived from ESM-1, in combination with one or more pharmaceutically compatible vehicles. The pharmaceutical compositions according to the invention include those suitable for topical, oral, rectal, nasal or parenteral (including intramuscular, subcutaneous and intravenous) administration or in a form suitable for administration by inhalation or insufflation. The pharmaceutical compositions according to the invention may be presented in the form of unit doses and may be prepared by any method well known to a person skilled in the art of pharmaceutical medicine All the methods include a step consisting of combining the antagonist compound comprising the active principle of the composition with a liquid vehicle or a finely divided solid vehicle and, if necessary, forming the product, for example in the form of tablets or capsules.

For oral administration, a pharmaceutical composition according to the invention is preferably presented in the form of dose units such as tablets, capsules or hard capsules. When it is presented in a form contained in a pressurized container, the pharmaceutical composition may contain a propellant such as dichlorodifluoromethane, trichlorofluoromethane, dichlorotetrafluoroethane, carbon dioxide or other appropriate gases. In the case of a pressurized aerosol, the dose unit may be provided with a valve able to supply a given quantity of the pharmaceutical composition.

According to another embodiment, the pharmaceutical composition according to the invention may be in the form of a dry powder composition for administration by inhalation or insufflation, for example in the form of a mixture of a powder of the antagonist compound and of a suitable base powder, such as lactose or starch. The powder composition may be presented in a dose unit, for example in s the form of capsules or dispensers from which the powder may be administered using an inhaler or insufflator device.

A solid pharmaceutically acceptable vehicle compatible with a pharmaceutical composition according to the invention includes substances such as flavouring agents, lubricants, solubilizing agents, suspension agents, fillers, compression auxiliaries, binders or dispersion agents as well as encapsulating materials. In the powders, the vehicle is a finely divided solid which is in admixture with the antagonist compound of ESM-1 also in a finely divided form. In the tablets, the active principle antagonist of ESM-1 is mixed with a vehicle having suitable compression properties and compacted into the desired form and size. The powders and tablets preferably contain less than 99% of the active principle. The preferred solid vehicles are for example calcium phosphate, magnesium stearate, talc, sugars, lactose, dextrin, starch, gelatine, cellulose, polyvinylpyrrolidone and the ionexchange resins.

Liquid vehicles are used to prepare a pharmaceutical composition according to the invention in the form of a solution, a suspension, an emulsion, a syrup, an elixir and a pressurized composition. The active principle antagonist of protein ESM-1 may be dissolved or suspended in a pharmaceutically acceptable vehicle such as water, an organic solvent, or a mixture of the two or pharmaceutically acceptable oils or fats. The liquid vehicle may contain other pharmaceutically acceptable additives such as solubilizing agents, emulsifiers, buffers, preservatives, sweeteners, flavouring agents, suspension agents, thickening agents, colorants, viscosity regulators, stabilizers or osmo-regulators. Illustrative examples of liquid vehicles for oral and parenteral administration include water, alcohols, (including monohydric and polyhydric alcohols such as the glycols), oils such as coconut oil or fractionated peanut oil. For parenteral administration, the vehicle may also be an ester such as ethyl oleate and isopropyl myristate. Liquid pharmaceutical compositions in the form of sterile solutions or suspensions may be used for intramuscular, intraperitoneal or subcutaneous injection.

A pharmaceutical composition according to the invention preferably contains from 1 to 1000 mg of antagonist compounds of protein ESM-1 per dose unit, and preferably from 10 to 500 mg of antagonist compound of protein ESM-1 per dose unit.

The present invention also concerns a method of treatment and/or prevention of a cancer comprising a step during which a pharmaceutical composition such as defined above is administered to a patient having need of such treatment.

Pharmaceutical Composition Containing an Antagonist Compound of Protein ESM-1 of the Antisense Polynucleotide Type.

Also forming part of the invention are pharmaceutical compositions containing a therapeutically effective quantity of an antagonist compound of protein ESM-1 of the antisense polynucleotide type as defined in the present description in addition to methods of treatment and/or prevention of a cancer comprising the administration to a patient having need of such a treatment of a pharmaceutical composition containing an antisense polynucleotide such as defined above.

An antisense oligonucleotide according to the invention may be administered by any means, either local or systemic.

The local administration of an antisense polynucleotide of the invention, for example in the tumour, may be performed by the administration of the antisense polynucleotide directly into the tumour or into the tissue surrounding the tumour so that the oligonucleotide can migrate to, and where appropriate enter into, the tumour cells. For example, the antisense polynucleotides may be injected using a syringe. The injection may be intramuscular, intravenous, intraperitoneal or subcutaneous. The antisense polynucleotide may be administered to the liver via the hepatic portal vein. Similarly, the antisense polynucleotide may be administered to the lung using an inhalation device.

Other means of administration of an antisense polynucleotide may be used. For example, the antisense polynucleotides may administered systemically after their insertion into an expression vector. The term "expression vector" includes a plasmid, a virus or any other vehicle known in the state of the art to ensure the expression of an antisense polynucleotide.

For the use of vectors suitable for the recombinant expression of an antisense polynucleotide, a person skilled in the art may advantageously use the vectors pMSXND described by LEE and NATHANS (1988), eukaryotic virus vectors, such as those described by GLUZMAN (1982), or the adenoviruses and adeno-associated viruses such as those described in the U.S. Pat. Nos. 5,173,414 and 5,354,678 or an expression system including an expression vector described by MOXHAM et al. (1993).

The expression vector preferably contains a promoter allowing the production of the antisense polynucleotide in an animal, preferably a mammal, and preferably in humans, such as the polyhedrin promoter.

The expression vector may be suitable for the targeted expression of the antisense polynucleotide at the site of the tumour, for example by placing the nucleic acid coding for the antisense polynucleotides under the control of a promoter specific to certain cells, such as the epithelial cells or the endothelial cells. An example of such a promoter is the viral promoter designated NuNTV which is specifically useful in the treatment of breast cancers. Other examples of such specific promoters are milk protein promoters such as β-lactoglobulin, α-casein and β-casein.

The therapeutically effective quantity of an antisense polynucleotide of the invention may be determined as the quantity necessary for a significant reduction of the translation of protein ESM-1 at the systemic or local level.

It will be clear to a person skilled in the art that the therapeutically effective concentration of the antisense potynucleotide varies with the choice of the mode of administration. For example, if the antisense polynucleotide is administered by injection to a mammal, the dose unit comprises a syringe containing an effective quantity of the antisense polynucleotide. An effective quantity of the antisense polynucleotide for a systemic administration is between 0.01 mg/kg and 50 mg/kg administered once or twice per day. A therapeutically effective quantity of an antisense polynucleotide according to the invention included in a pharmaceutical composition is generally between $10^4$ and $10^{11}$ molecules of antisense polynucleotide per administration and preferably between $10^5$ and $10^{10}$ molecules of DNA per administration.

However, different dosage protocols may be used according to (i) the individual capacity of the antisense polynucleotide to inhibit the expression of protein ESM-1, (ii) the severity or extent of the disease, or (iii) the pharmacokinetic behaviour of the antisense polynucleotide used.

The antisense polynucleotide may be combined with a pharmaceutically acceptable vehicle or an excipient. Examples of excipients include fillers, binders, dispersion agents, lubricants, according to the type of administration and the forms of dosage. Preferred forms of dosage include liquid solutions, advantageously physiologically compatible buffers such as HANK's or RINGER solutions. In addition, the antisense polynucleotides according to the invention may be formulated in a solid form then redissolved or resuspended immediately before use. This includes lydphilized forms and liposomes containing such antisense polynucleotides.

An antisense polynucleotide of the invention may also be systemically administered by the transmucosal, transdermal or oral routes. For the transmucosal or transdermal routes of administration, penetrating agents may be used in formulation such as bile salts or derivatives of fusidic acid.

The present invention also relates to a method of treatment and/or prevention of a cancer comprising a step of administration, to a patient having need of such treatment, of a pharmaceutical composition such as defined above containing an antagonist compound of ESM-1 of the antisense polynucleotide type.

In general, any of the pharmaceutical compositions of the invention such as defined above and containing a therapeutically effective quantity of an antagonist compound of protein ESM-1 is useful in the prevention and/or treatment of a cancer.

As a non-limiting illustration, a pharmaceutical composition according to the invention is useful for the prevention and/or treatment of cancers such as cancers of the respiratory tracts, broncho-pulmonary cancers, breast cancers, cancers of the colon and renal cancers as well as cancers of the digestive system.

The present invention is in addition illustrated, without in any way being limited, by the following examples and figures.

FIGURES

FIG. 1 illustrates Western Blot immunoblotting gels and colorations of ESM-1 on SDS-PAGE gel.

Each immunoblotting gel was revealed with the anti-ESM-1 monoclonal antibody MEP14. The second anti-mouse antibody marked with horseradish peroxidase was purified by affinity and gave negative results when used alone.

FIG. 1A. Immunoblotting gel of protein ESM-1 from different cell types expressing this protein.

The immuno-precipitation of ESM-1 from cell culture supernatants SVI (1), 293-ESM(2) and CHO-ESM(3) was performed with the antibody MEP19 when this is indicated, or with a control antibody. The arrows show the band specific to ESM-1. The native form of ESM-1 is represented by a diffuse band around 50 kD.

FIG. 1B. Absence of detection of purified protein ESM-1 with coomassie blue.

5 μg of protein ESM-1 purified from SVI cells was loaded onto an SDS-PAGE gel at 15% and coloured with coomassie blue in order to detect the peptide part of the molecule. The arrows show the absence of detection of ESM-1.

FIG. 1C. Detection of purified protein ESM-1 with alcian blue.

5 μg of protein ESM-1 purified from SVI cells was loaded onto an SDS-PAGE gel at 15% and revealed with alcian blue in order to detect the glycan part of the molecule. The arrow shows protein ESM-1.

FIG. 2 illustrates the apparent molecular weight of the peptide and glycan parts of ESM-1.

FIG. 2A Analysis by mutation of the site of fixation of O-glycosylation.

Two presumed O-glycosylation sites (threonine 120 and serine 137) were substituted by an alanine residue by directed mutagenesis. The wild-type protein ESM-1 (VT), the ESM-1 T120A and S137A mutants, and negative controls (MOCK) were transfected in 293 cells and the cell culture supernatants and cell lysates were analysed by immunoblotting (Western-Blot) using monoclonal antibody MEP14. The arrows show the specific bands, FIG. 2B. Effect of a treatment with proteinase K on ESM-1.

Protein ESM-1 purified from SVI (1) and 293-ESM cells (2) was digested by proteinase K and loaded onto an SDS-PAGE gel at 15% The upper arrow shows the wild type of untreated protein ESM-1 and the lower arrow shows protein ESM-1 digested by proteinase K.

FIG. 3 illustrates the effects of specific chondroitinases on ESM-1.

FIG. 3A. Treatment of purified wild-type protein ESM-1 with chondroitinase ABC.

Secreted protein ESM-1 was purified by ion-exchange chromatography, followed by immunoaffinity chromatography from cell culture supernatants of SVI(1), 293ESM(2) and from human plasma (3), then digested or not by chondroitinase ABC. 50 ng of the digested protein were loaded onto an SDS-PAGE gel at 15% then analysed by immunoblotting (Western-Blot). The upper arrow shows the undigested forms of ESM-1 and the lower arrow the digested forms of ESM-1.

FIG. 3B. Treatment of purified wild-type protein ESM-1 with chondroitinase B.

Protein ESM-1 purified from cell culture supernatants of SVI (1) and 293-ESM(2) was digested or not by the chondroitinase. The proteins were loaded onto SDS-PAGE gel at 15%. The upper arrow shows the different undigested forms of ESM-1 around 50 kD and the lower arrow shows the different forms of digested ESM-1, around 22 kD.

FIG. 3C. Treatment of purified wild-type protein ESM-1 with chondroitinase AC.

Protein ESM-1 purified from cell culture supernatants of HUVEC (1) and 293-ESM(2) was digested by chondroitinase AC and loaded onto SDS-PAGE gel at 15%. The upper arrow shows the different undigested forms of ESM-1 around 502 kD and the lower arrow shows the different forms of digested ESM-1, around 22 kD.

FIG. 3D. Treatment of purified wild-type protein ESM-1 with chondroitinase C.

Protein ESM-1 purified from cell culture supernatants of HUVEC (1) and 293-ESM (2) was digested or not by chondroitinase C and loaded onto SDS-PAGE gel at 15%. The upper arrow shows the different undigested forms of ESM-14 around 52 kD and the lower arrow shows the different forms of digested ESM-1 around 22 kD.

FIG. 4 illustrates the effects of purified wild-type protein ESM-1 on the coagulation time in the presence of thrombin. The delay and the reduction of thrombin production can be seen for heparinized plasma and also for the four other curves (plasma rich in platelets or PRP: open diamonds; plasma rich in platelets+ESM-1 at 0.2 mg/ml: solid squares plasma rich in platelets+ESM-1 00.5 mg/ml: solid triangle; plasma rich in platelets+ESM-1 at 1 mg/ml: solid circle; plasma rich in platelets+heparin: open circle).

FIG. 5 illustrates the biological activity of the proteoglycan ESM-1 on the proliferation of 293 cells induced by factor HGF/SF. The stimulation of the incorporation of $^3$H-thymidine by 293 cells induced by factor HGF/SF was studied. The cells were sown at $1\times10^4$ cells per well in a DMEM medium supplemented with transferin and insulin and HGF/SF at 50 ng per ml before addition of different molecules. The bars represent the percentage increase in $^3$H-thymidine incorporation (mean+/−s.d. of triple samples of a representative experiment) in the presence of the additions shown of serum, different forms of ESM-1 at 2.5 mg/ml and decorin at 2.5 mg/ml. The background noise level of $^3$H-thymidine incorporation in the presence of HGF/SF was generally between 7.000 and 8.000 cpm per well. The results presented are similar to those obtained in three other separate experiments.

FIG. 6 illustrates a study of twelve responses of the different forms of ESM-1 and of decorin on the mitogenic activity induced by factor HGF/SF. The simulation of DNA synthesis by 293 cells was studied in the presence of HGF/SF at 50 nanograms per ml alone or in the presence of different concentrations of wild-type protein ESM-1/WT (open square), of mutant non-glycosylated protein ESM/S137A (solid circle), of the GAG chain derived from protein ESM/WT (solid square) or of decorin (open circle). The mean values of triplicate measurements of $^3$H-thymidine incorporation obtained in one experiment among three independent experiments are shown in FIG. 6. The results are expressed in cpm. The standard deviations were approximately 10%.

FIG. 7 illustrates the tumorigenic power of protein ESM-1. Two batches of more than 10 mice received control HEK cells or cells transfected with a vector coding for the cDNA of wild-type protein ESM-1 (ESM/WT). On FIG. 7A, the percentage of tumours macroscopically visible at the eighth week at the injection point and whose tumoral volume was more than 1 cm$^3$ is shown as ordinate. FIG. 7B illustrates the kinetics of appearance of the tumours in mice having received transfected HEK expressing glycosylated protein ESM-1 (ESM/WT). The number of weeks after injection of the cells is given on the abscissa. The mean tumoral volume, expressed in cm$^3$, is given on the ordinate.

FIG. 8 illustrates the production of ESM-1 by tumours induced in mice.

FIG. 8A represents the serum level of protein ESM-1 found in the two batches of mice, at the eighth week following the injection of the cells. The abscissa shows respectively the batch of mice having received the control HEK cells and the batch of mice having received the HEK cells expressing glycosylated protein ESM-1 (ESM/WT). The serum level of ESM-1 found, expressed in nanogram/ml, is given on the ordinate.

Figure 9A:
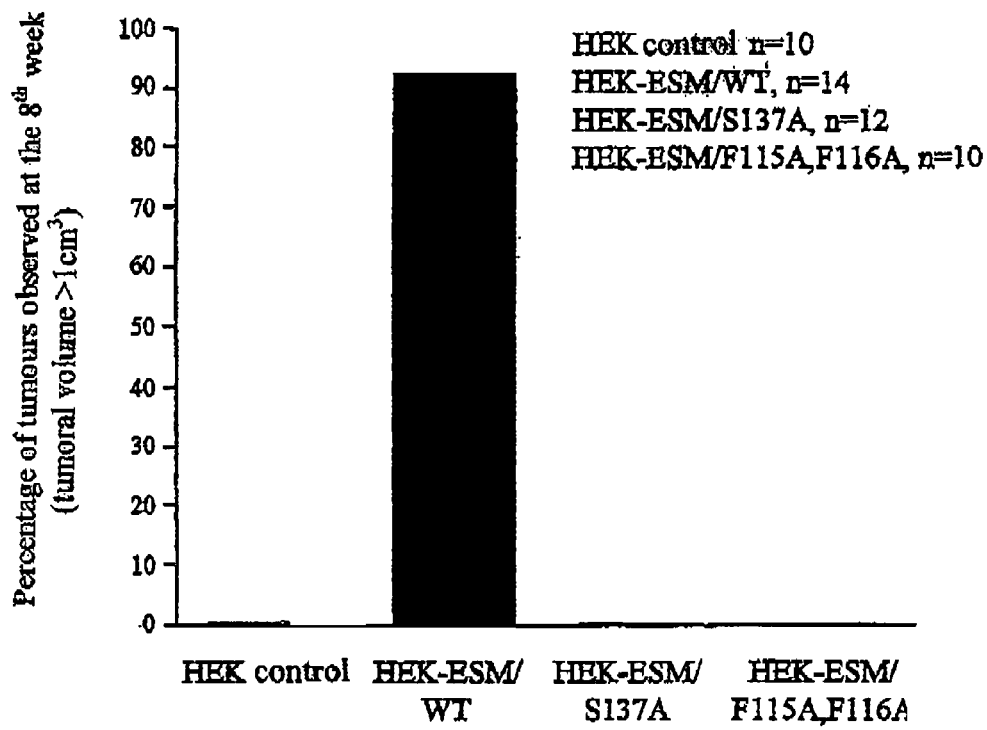
FIG. 9 illustrates the tumorigenic activity of the different forms of protein ESM-1.

FIG. 9A illustrates the appearance of tumours in different batches of mice, the mice having received respectively control HEK cells, HEK cells transfected with a cDNA coding for glycosylated protein ESM-1 (ESM/WT), cells transfected with nonglycosylated protein ESM-1 (ESM/S137A) and HEK cells transfected with a cDNA coding for protein ESM-1 replaced in positions 134 and 135 (ESM/F115A, F116A). The ordinate shows the percentage of tumours macroscopically visible at the eighth week at the point of injection whose tumoral volume was greater than 1 cm$^3$.

Figure 9B:
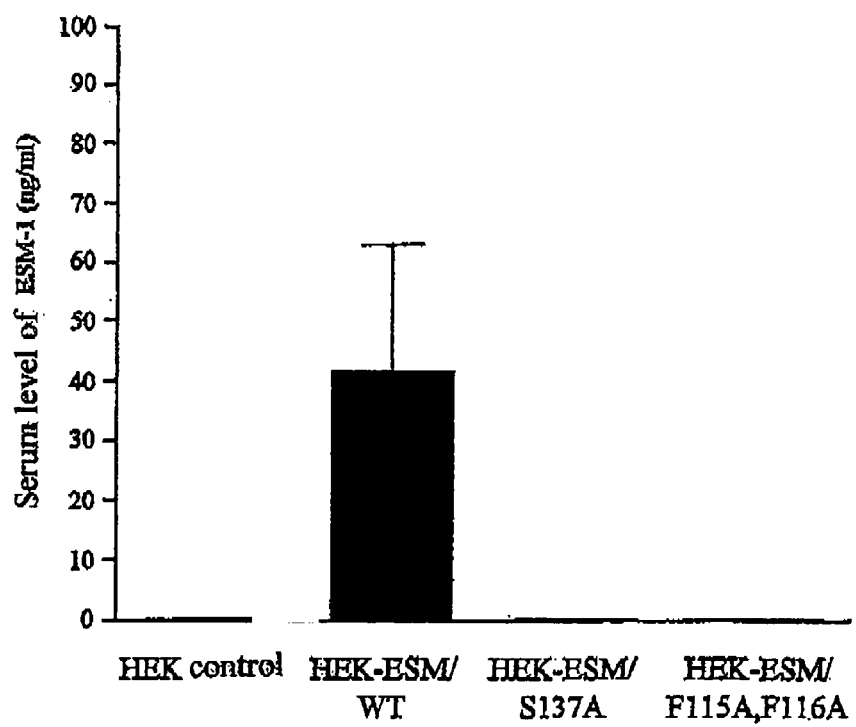

FIG. 9B illustrates the serum level of ESM-1 in the different identical batches of mice. The serum level of ESM-1, expressed in nanogram/ml, is given on the ordinate.

Figure 10:
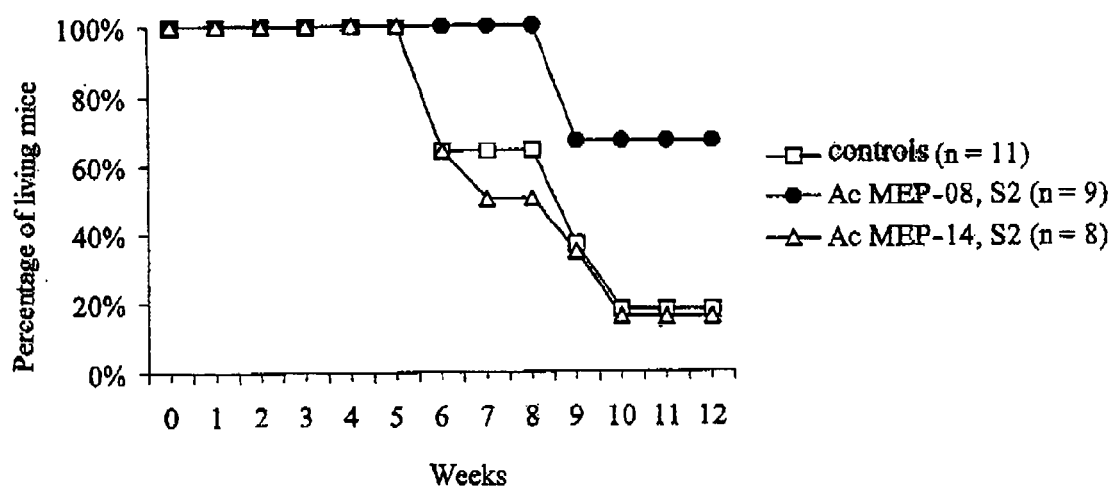

FIG. 10 illustrates the inhibiting effect of the monoclonal antibody MEP08 on the pro-tumoral activity of protein ESM-1.

The injection of MEP-08 antibodies increased the survival of mice from the HEK ESM/WT group. The monoclonal antibodies MEP-08 were injected intraperitoneally at a dose of 400 µg from the second following the inoculation of the HEK/ESM-WT cells. The injections were repeated weekly for 12 weeks. A control antibody, MEP-14, was used under the same conditions. The mice were sacrificed when their tumoral volume was greater than 6 cm$^3$. (n>8 mice in each group). The figure shows the percentage of surviving mice in each of the groups.

EXAMPLES

Example 1

Post-translational Modification of the Secreted Form of Protein ESM-1

A. Materials and Methods

A.1 Cell Culture and Materials

CHO cells were cultured in a culture medium MAMα (Gibco BRL, Life Technologies, France) supplemented with 10% foetal calf serum. Human endothelial cells transfected by the virus SV40, the SVI cells described by LASSALLE P et al. (1992), were cultured in a medium RPMI 1640 containing 2 mM of L-glutamine and 10% foetal calf serum. Human embryo kidney cells, the cells of the line 293, were cultured in a medium DMEM from Dulbecco with 10% foetal calf serum. The human embryo kidney cells, the cells of the line 293, used for the proliferation test were cultured in modified EAGLE medium from Dulbecco (Gibco BRL) supplemented with insulin at 10 mg/ml and transferin at 10 mg/ml. The proteinase and chondroitinase ABC were commercially available from Boehringer Mannheim. Chondroitinases B, AC and C are marketed by Sigma. Human factor HGF/SF is marketed by R & D and decorin by Sigma. Anti-ESM-1 monoclonal antibodies were produced and purified as described by BECHARD et al. (2000).

A.2 Development of Cell Lines Expressing ESM-1.

The complete cDNA coding for ESM-1 was directed, purified and inserted into the expression vector pcDNA3 (marketed by Invitrogen) between the XhoI and HindlIII sites. The vector constructions were transfected in the cell lines CHO and 293 in the presence of lipofectamine (GIBCO BRL), then selected on G418 (1000 μg/ml for the CHO line and 300 μg/ml for the 293 line). The cell lines which had been transfected stably were obtained by limiting dilution and the cells thus selected were designated respectively CHO-ESM and 2936-ESM.

A.3 Determination of the Site of O-lycosylation of ESM-1 by Mutation Analysis.

2 Potential sites of Olycosylation had been predicted using the software NET 0 glyc:0 Prediction Serveur.

The serine residue in position 137 (SEQ ID N°1) and the threonine in position 120 (SEQ ID N°1) were substituted by an alanine residue. The O-glycosylation mutants were produced by PCR using the mutagenesis kit Quick Change according to the manufacturer's recommendations (Stratagene).

The mutant cDNAs were confirmed by sequencing (sequencer ABI prism 377 from Applied Biosystems). The 293 cells were then transfected with the vectors into which the mutant cDNAs had been inserted to obtain the transitory and stable transfectants, respectively the 293-ESM/S 137A and 293-ESM/T120A.

A.4 Purification of the Proteoglycan ESM-1 Chondroitin/dermatan Sulfate.

The cell culture supernatants were adjusted to pH8, then passed over a column of DEAE-Sepharose (Pharmacia), washed with a Tris buffer 50 mM (pH8), 0.2 M NaCl, then eluted with a buffer Tris 50 mM (pH8), 0.8 M NaCl.

The eluates were adjusted to 50 mM Tris (pH8), 0.5 M NaCl and passed over an affinity column. The affinity column was composed of anti-ESM-1 monoclonal antibodies (produced by the hybridoma line MEC4) immobilized on a Affigel Hz hydrazide gel, according to the manufacturer's recommendations (Biorad).

After a washing step with a Tris buffer 50 mM (pH8), M NaCl 0.5, protein ESM-1 was eluted with a solution of 3M MgCl$_2$, concentrated and dialysed against the same buffer on an ultrafree 30 device (millipore).

The eluted material was then quantified by immunodetection with anti-ESM-1 antibodies, and checked on SDS-PAGE using a coloration with coomassie blue or alcian blue.

The purification of protein ESM-1 from human plasma was performed according to the following protocol.

800 ml of plasma supplied by the blood transfusion agency (Lille, France) were precipitated with a 60% ammonium sulfate solution and dialysed against a Tris buffer 50 mM (pH 8), 0.5 M NaCl. The precipitated and dialysed plasma extract was then passed over a 50 ml pre-column of the Affigel type (Biorad) before a passage over an anti-ESM-1 immunoaffinity column. The protein ESM-1 fixed on the immunoaffinity column was recovered as described below.

The non-glycosylated form of ESM-1 (ESM/S137A) was purified in a single step by chromatography and immunoaffinity. The degree of purity of glycosylated protein ESM-1 (ESM/WT) and of the non-glycosylated protein replaced on serine 137 (ESM/S137A) was checked by FPLC. The purified material was free from endotoxins, as proved by the results of a limulus amebocyte lysate test (BIOwhitaker).

A.5 Immunoprecipitation, Immunoblotting and Sequencing.

The size of the different forms of ESM-1 was determined by immunoprecipitation and immunoblotting from cell culture supernatants and cell lysates. The cells were lysed in a buffer containing 0.5% of NP40, a cocktail of anti-proteases (Boehringer Mannheim, Germany) in PBS for 30 minutes at 4° C. with agitation.

The lysates were then centrifuged at 10.000 g for 15 min in order to obtain the clarified cell lysates.

The culture supernatants were filtered over a filter having a pore diameter of 0.45 mm.

1 μg of ESM-1 monoclonal antibody produced by the hybridoma line MEP19 or 1 μg anti-ICAM-1 monoclonal antibody (clone 164B) was added to the clarified lysate or to the cell culture supernatant and incubated overnight at 4° C. with agitation.

50 μl of an anti-mouse immunoglobulin conjugated with agarose beads (sigma) were added at 4° C. over 90 min, before centrifugation and washing with a lysis buffer and washing in PBS.

The beads were resuspended in 20 and 40 μl of SDS-PAGE buffer for 5 min, centrifuged, and the supernatants were analysed.

The samples were subjected to electrophoresis on SDS-PAGE gel, then transferred onto a nitrocellulose membrane using standard procedures.

After a blocking step, the membranes were incubated for one hour with 1 μl of an ESM-1 monoclonal antibody produced by the hybridoma line MEP14, washed, then incubated for 1 hour with an anti-Fc mouse secondary antibody conjugated with horseradish peroxidase (marketed by SIGMA). After several washings revelation was performed using the detection kit ECL marketed by Amersham.

For amino acid sequence analysis, purified protein ESM-1 was subjected to electrophoresis on SDS-PAGE gel, then electrotransferred onto a polyvinylidene difluoride membrane (PVDF) marketed by MILLIPORE, then coloured using 0.1% coomassie blue. The protein band at 50 kD was excised from the membrane and the N-terminal sequence was determined by EDMAN degradation on a protein sequencer of type ABI 473A.

A.6 Digestion of the Peptide Part of ESM-1 by Proteinase K

In order to determine the size of the glycosaminoglycan, purified protein ESM-1 was digested with proteinase K with an enzyme:ESM-1 ratio of 1:50 (w/w) in a Tris buffer 10 mM, pH8, in the presence or absence of 0.1% SDS at 56° C. for 3 hours. A quantity of bovine serum albumin (BSA) 10 times?? greater than that of the protein ESM-1 was digested by proteinase K in order to verify its complete degradation. The samples were analysed on a 12% SDS-PAGE gel, followed by coloration with coomassie blue and alcian blue.

A.7 Digestion of ESM-1 by Chondroitinases ABC, B, AC and C

In order to analyse the nature of the substitution of the glycosaminoglycan, purified protein ESM-1 was digested with several chondroitinases: chondroitinases ABC (0.5 units/mg in buffer 100 mM TrisHCl, pH 8. 30 mM sodium acetate, pH 5.2 at 37° C. for 45 min), chondroitinase B (200 units/mg in buffer 20 mM Tris-HCl, 50 mM NaCl, 4 mM $CaCl_2$, 0.01% BSA, pH 7.5 at 25° C. for two hours), chondroitinase AC (one unit per ml in buffer 250 mM Tris HCl, 75 mM sodium acetate, pH 7.3 at 37° C. for two hours), chondroitinases C (80-120 units/ml in buffer 50 mM Tris HCl , pH 8 at 25° C. for 3 hours). The samples were analysed by immunoblotting.

A.8 Anti-coagulant Activity.

The control plasma poor in platelets (PPP) was prepared from blood in the presence of the anticoagulant sodium citrate (30 mM), by centrifugation at 2500 g for 15 min. All the reagents were marketed by STAGO Diagnostica (France). Three parameters were evaluated, by adding protein ESM-1, buffer or heparin to the platelet-poor plasma.

a) APTT (Activated Partial Thromboplastin Time): this parameter explores the intrinsic route of blood coagulation (FI, FII, FV, FVIII, FIX, FX, FXI, FXII). The deficit or inhibition of one of these factors increases the coagulation time of the mixture PPP reagent, cephalin, activator, $CaCl_2$.

b) TCT (Thrombin Clotting Time): this parameter is analysed on a mixture of platelet-poor plasma (PPP) in the presence of thrombin. With a standard concentration of thrombin, the coagulation time of the plasma is constant. Defects in the formation of fibrin induce an increase in the coagulation time.

c) anti-Xa activity: the anti-Xa activity of heparin or other inhibitors acting on factor FXa is detected by a competitive test. The sample studied (PPP+ESM-1, +buffer or +heparin) is mixed with factor Fxa and a specific chromogenic substrate of factor Fxa. The final coloration is inversely proportional to the concentration of inhibitor.

A.9 Test of Thrombin Generation

This sensitive global test can detect defects in plasma or platelets inducing a delay or a reduction in thrombin generation. A plasma rich in platelets (PRP) was prepared from blood in the presence of sodium citrate by centrifugation at 150 g for 10 min. The thrombin generation test was performed, for each of the subjects, in samples in the absence of ESM-1, with non-fractionated calcium heparinate (0.5 Ul of anti-Xa/ml) or with 0.2 mg/ml, 0.5 mg/ml and 1 mg/ml of ESM-1 (final concentration).

The protein ESM-1 was added 10 min before the test.

At 37° C., 1 ml of plasma was mixed with 1 ml of $CaCl_2$ and a chronometer was started. Aliquot fractions of 0.1 ml were taken from the reaction mixture each minute for 1 min.

The clot formed in the reaction mixture was regularly removed. The aliquot fractions were mixed with 0.2 ml of fibrinogen (Sigma, 4/1000 in an Owren buffer at 37° C. and the coagulation time was measured for each of the aliquot fractions).

The thrombin formed in the reaction mixture acts of the forminogens, inducing the formation of fibrin. The coagulation activity was maximal between 4 and 8 min then reduced due to the neutralization of the thrombin by the anti-thrombin.

A.10 Analytical Chromatography by Gel Filtration

50 µg of purified glycosylated ESM-1 (ESM/WT) and of purified non glycosylated ESM-1 (ESM/S137A) in 50 mM Tris buffer, pH 8.5, 0.5 M NaCl were separated by liquid chromatography on a Superdex 200 column (for ESM/WT) or Superdex 75 (for ESM/S137A) marketed by Pharmacia, using the chromatography system Biorad Biologic Chromatography System with a flow of 1 ml/min.

As standard, the following calibration kit of high and low molecular weight (Pharmacia Biotech) was used, ribonuclease A (bovine pancreas, 13.7 kD), ovalbumin (43 kD) albumin (bovine serum, 67 kd), aldolase (rabbit muscle, 158 kD), ferrtine (horse spleen, 440 kD), thiroglobulin (bovine thyroid, 669 kD).

The molecular weight standards were separated using a buffer identical to that used for the proteins ESM-1 and the separation was performed immediately after the separation of the proteins ESM/WT and ESM/S137A. The elution time of the standard proteins was used to draw a standard linear curve, Kav=f(log MR) in order to determine the apparent molecular weights of the proteins ESM/WT and ESM/S137A respectively.

Fractions of 1 ml were collected an protein ESM-1 was detected using a specific immunoenzymatic test (ELISA).

B. Results

B.1 Post-translational Modifications of the Secreted Form of Protein ESM-1 Produced by Endothelial Cells and by Established Cell Lines.

In order to determine whether ESM-1 was matured as a secreted molecule, as suggested by the presence of an N-terminal amino acid sequence predicted as a signal peptide, protein ESM-1 was purified from the cell line 293-ESM.

The N-terminal sequence of the 50 kD form indicated that the signal peptide of 19 amino acids was cleaved at the predicted site, resulting in a mature polypeptide of ESM-1 of 165 amino acids beginning at the tryptophan residue in position 20 of sequence SEQ ID N°1, the N-terminal sequence being WSNNYAVD-P.

ESM-1 was immunoprecipitated from culture supernatants of HUVEC, SV1, 293-ESM and CHO-ESM cells, the analysed by immunoblotting.

It had previously been shown that in HUVEC cells supernatants, ESM-1 migrated in the form of a diffuse band at around 50 kD.

Figure 1:
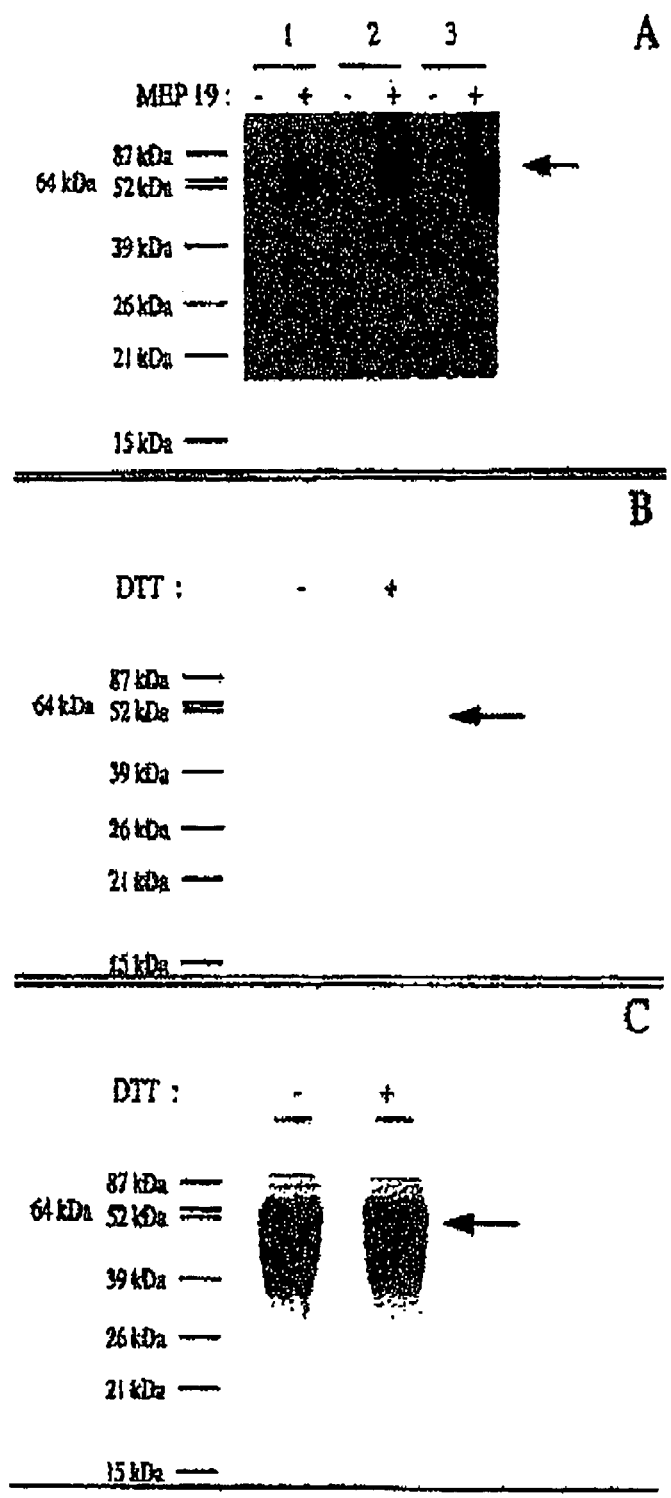

A band similar in size was observed with the supernatants of SV1, 293-ESM and CHO-ESM cells (FIG. 1A).

The molecular weight found was larger than the predicted molecular weight. This result suggested that the secreted form of ESM-1 had undergone post-translational modifications. The fact that purified protein ESM-1 was better coloured on SDS-PAGE gel with alcian blue than with coomassie blue suggested that ESM-1 was glycosylated (FIGS. 1B, 1C) rather than oligomerized across the disulfide bridge, because reductive conditions did not modify the apparent molecular weight of ESM-1.

B.2. The Serine Residue in Position 137 (SEQ ID N°1) is the Site of O-glycosylation of ESM-1.

A computer analysis of the potential glycosylation sites identified three putative sites of Olycosylation, respectively on the serine in position 16, on the threonine in position 120 and on the serine in position 127, but no site of N-glycosylation.

The threonine residue in position 120 and the serine residue in position 137 were replaced by an alanine residue.

These mutants were transitorily expressed in the 293 cells.

Protein ESM-1 was then immunoprecipitated from cell lysates and culture supernatants, and analysed by immunoblotting.

Figure 2:
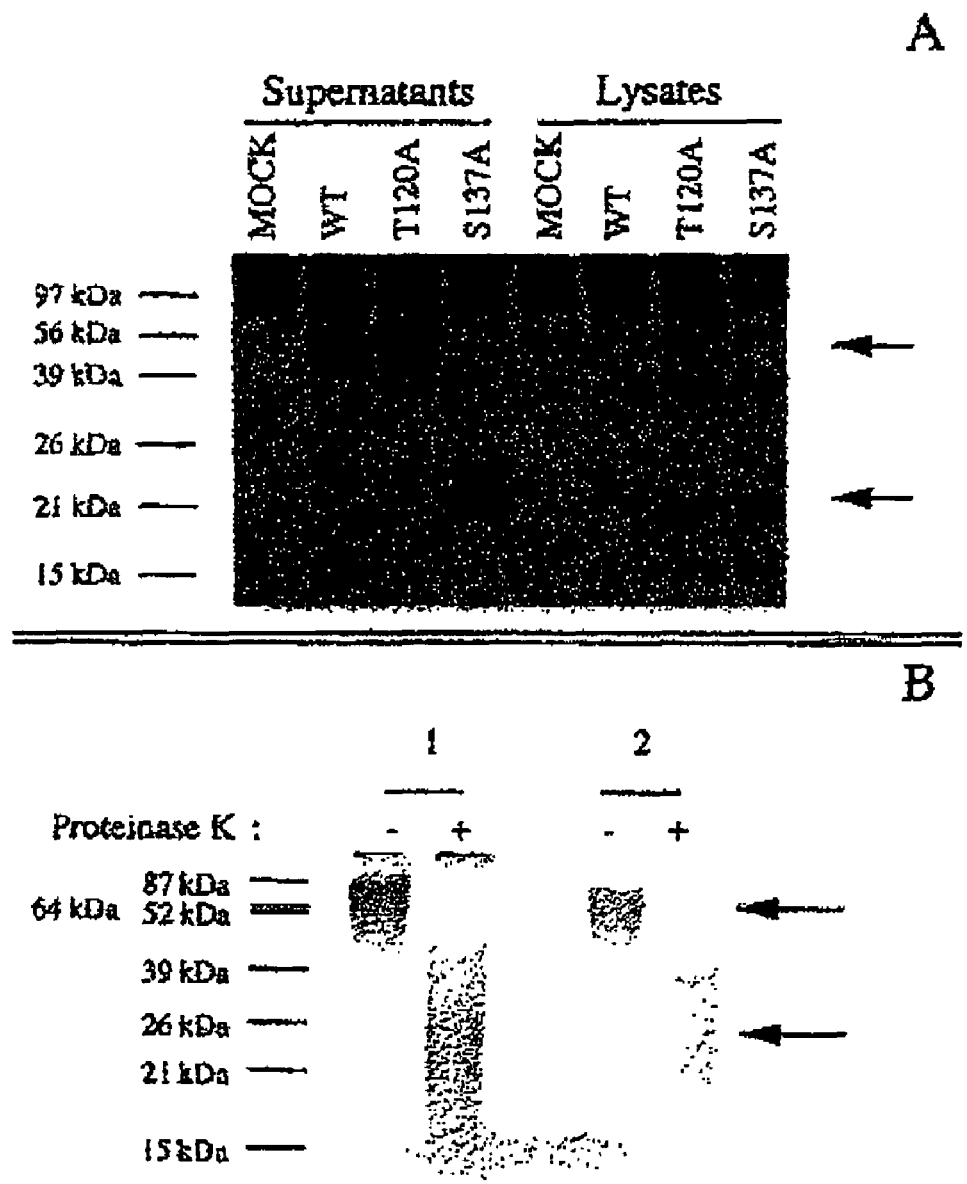

Protein ESM/T120A migrated at 50 kD, at a position similar to the apparent molecular weight of the wild form of ESM-1 (ESM/WT), as shown on FIG. 2A.

In contrast, protein ESM/S137A migrated at 22 kD corresponding to the intracellular form of ESM-1 (FIG. 2A), a molecular weight compatible with the predicted molecular weight of ESM-1.

The immunoprecipitations performed from transitorily transfected COS and CHO cells gave the same results, showing that only the serine residue in position 137 constituted a site of glycoconjugation in all the cell models studied.

In order to determine the length of the glycosaminoglycan (GAG) of ESM-1, the peptide part of ESM-1 was completely digested by proteinase K.

The treatment by proteinase K caused a change in the molecular weight from 50 kD to 25-30 kD (FIG. 2B). These results show that the band of apparent molecular weight at 50 kD is compatible with the presence of a polypeptide of 22 kD which is glycoconjugated on the serine in position 137 by a GAG chain of a mean size of 25-30 kD.

B.3 The GAG Chain of ESM-1 is Sensitive to Chondroitinase ABC

In order to characterize the GAG chain of ESM-1, protein ESM-1 was first digested by chondroitinase ABC. The treatment by chondroitinase ABC reduced the molecular weight of secreted protein ESM-1 to 22 kD (FIG. 3A), suggesting that the carbohydrate of ESM-1 is a chain of the chondroitin type.

Figure 3:
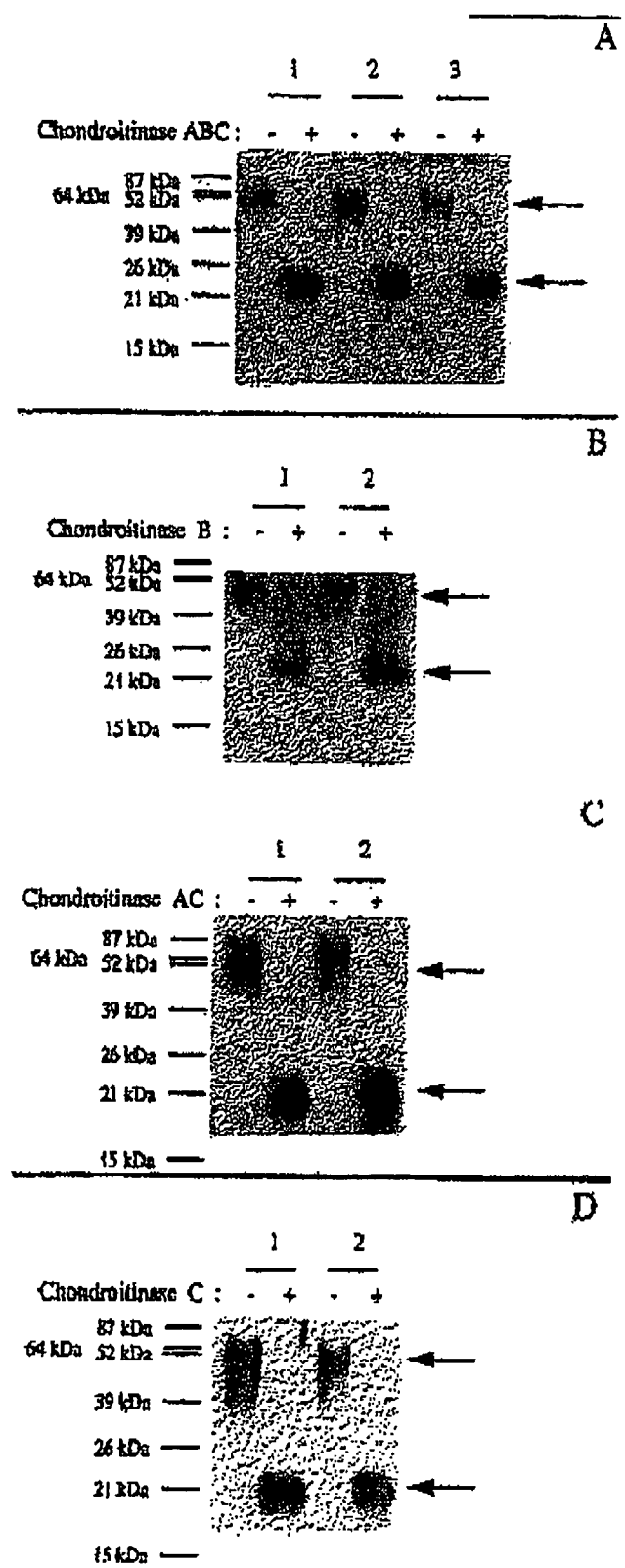

The profile is similar with protein ESM-1 purified from 293-ESM cells and from the human endothelial cell line SVI. Because protein ESM-1 circulates in the blood, we also studied the behaviour of protein ESM-1 purified, from human plasma. The results showed a single principal band of 50 kD, which had a molecular weight of 22 kD after treatment with chondroitinase ABC, as for all the other cell lines studied (FIG. 3A). Thus protein ESM-1 is a soluble proteoglycan containing a single chondroitin sulfate chain.

B.4 The GAG Chain of ESM-1 is a Heterogeneous Chondroitin/dermatan Sulfate Chain.

In order better to determine the type of saccharidic unit which constituted the GAG chain of ESM-1, several specific enzymes were used, such as chondroitinases B, AC and C.

The treatment with chondroitinase B reduced the apparent molecular weight from 50 kD to 22 kD (FIG. 3B).

A similar profile was observed after treatment of ESM-1 by chondroitinases AC and C (FIGS. 3C, D).

These different enzymatic treatments showed that the GAG chain of ESM-1 contained different component units including a type of amino sugar, N-acetylgalactosamine, coupled to a differently sulfated iduronic or glucuronic acid.

These different units alternated in the chain, and were present at the beginning of the chain, close to the N-terminal disulfated dissacharides which persisted in the protein part after digestion by the chondroitinase, because all the treatments with chondroitinase lead to the same reduced apparent molecular weights of 22 kD.

B.5 Biological Activity of the Soluble ESM-1 Proteoglycan on Coagulation

Because protein ESM-1 is a secreted as a proteoglycan of the chondroitin/dermatan sulfate type by endothelial cells, and the dermatan sulfate shows effects on thrombin generation in vitro DELORME et al., (1996) and on coagulation, the anticoagulant potential of ESM-1 was verified using the parameters APTT, TCT, anti-Xa activity and on thrombin generation.

The results are given in table 1 below.

TABLE 1

Biological activity of the ESM-1 proteoglycan on coagulation

| | APTT (dry) | TCT (dry) | Activity Anti-Xa (UI/ml) |
|---|---|---|---|
| PPP + buffer | 30.6 | 16.5 | 0 |
| PPP + ESM-1 (0.2 µg/ml) | 30.8 | 17.5 | 0 |
| PPP + ESM-1 (0.5 µg/ml) | 31 | 18.8 | 0 |
| PPP + ESM-1 (1 µg/ml) | 31.8 | 20.7 | 0 |
| PPP + heparin | 89 | 39 | 0.45 |

The results in table 1 show that protein ESM-1 at different significant doses from 0.2 mg/ml to 1 mg/ml did not change the different parameters tested.

The parameters APTT, TCT and anti-Xa activity were similar for plasma poor in platelets (PPP) with the buffer or with protein ESM-1.

In the positive controls, the APTT, TCT and anti-Xa activities were higher for PPP in the presence of heparin.

Figure 4:
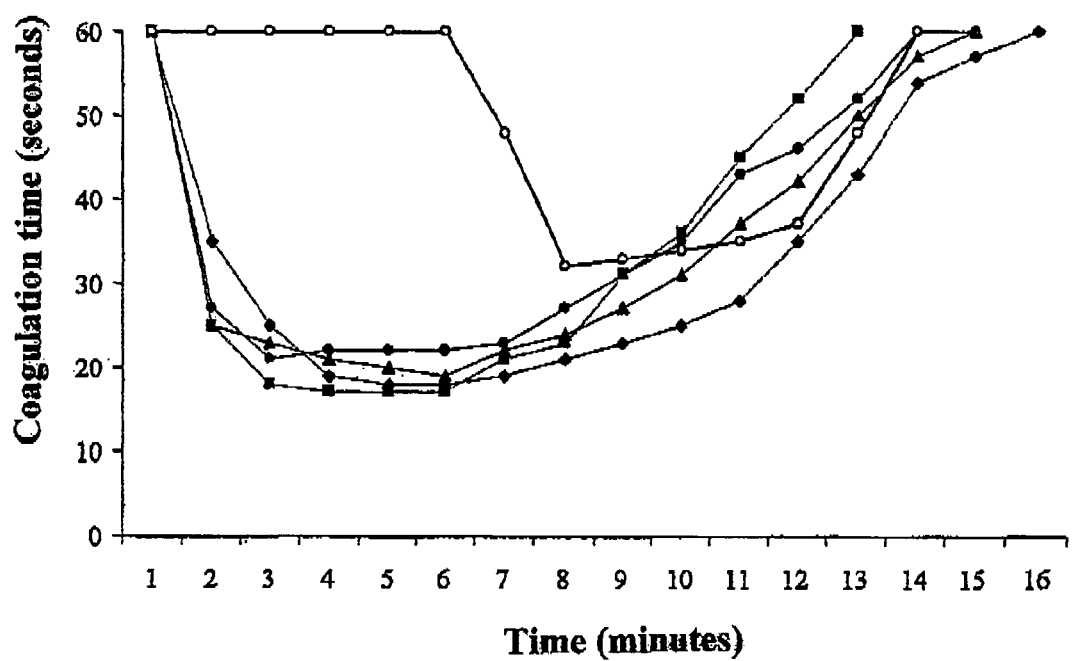

In addition, protein ESM-1 did not have an inhibitor effect on the thrombin generation test; no difference was observed according to concentrations of 0.2 mg/ml, 0.5 mg/ml and 1 mg/ml of ESM-1 compared to the control buffer, while heparin induced a delay in the formation of thrombin (FIG. 4).

Example 2

Effect of Protein ESM-1 onto the Mitogenic Activity of Factor HGF/SF

A. Materials and Methods

The activity of stimulation of proliferation was determined by measuring the incorporation of $^3$H thymidine by 293 cells.

The 293 cells were sown at a concentration of $1 \times 10^4$ cells per well in 96-well microplates of type TPP and maintained for 24 hours in DMEM culture medium supplemented with transferin and insulin.

The human recombinant HGF/SF was diluted in PBS containing 0.1% bovine serum albumin and added in water to 3 identical wells in order to obtain a final concentration of 50 ng/ml.

The recombinant proteins ESM/WT, ESM/S137A, the purified GAG chain derived from ESM-1 and decorin were added alone or in combination with factor HGF/SF at doses of from 1 ng/ml to 2.5 µg/ml, simultaneously with the addition of HGF/SF.

After 96 hours of culture, the cells were incubated with 0.5 µCi of $^3$H thymidine per well for 16 hours and incorporation of $^3$H thymidine was determined using a scintillation counter of the type Topcount Microplate Scintillation Counter (Packard).

The tests were performed on batches of three identical wells.

The cell viability was measured using the MTT reduction test.

B. Results

The effect of protein ESM-1 on the activity of factor HGF/SF was studied.

The incorporation of $^3$H-thymidine by. 293 cells was measured in the presence of HGF/SF at 50 ng/ml alone or in combination with different quantities of ESM/WT.

In a first batch of experiments, it was observed that HGF/SF alone at 50 ng/ml induced a proliferation of the 293 cells at a level equal to about 45% of the proliferation induced by the serum, while protein ESM/WT alone did not stimulate the proliferation of 293 cells.

Figure 5:
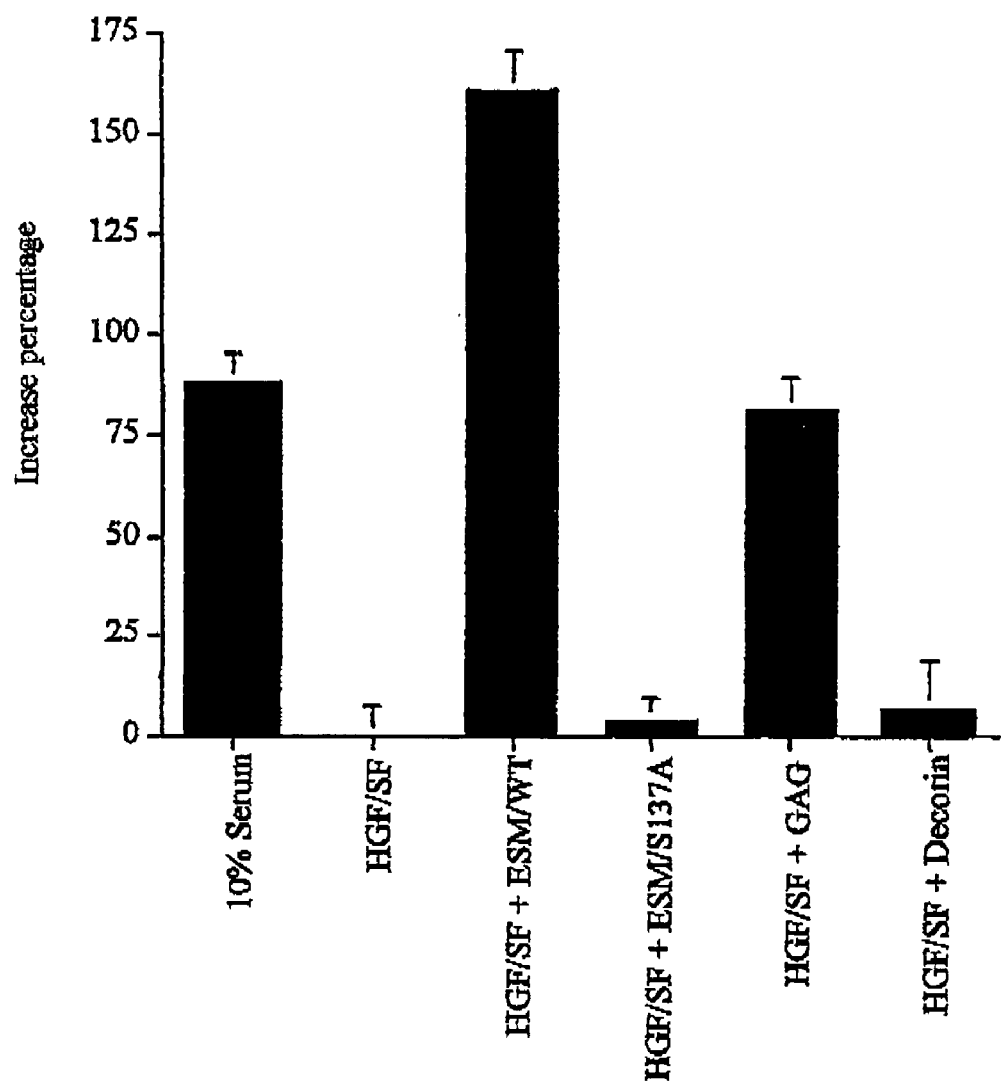

In contrast, when it was combined with factor HGF/SF, protein ESM/WT considerably increased the proliferation of 293 cells induced by HGF/SF with an increase of 162.3%, when the protein was tested at a concentration of 2.5 µg/ml (FIG. 5).

Figure 6:
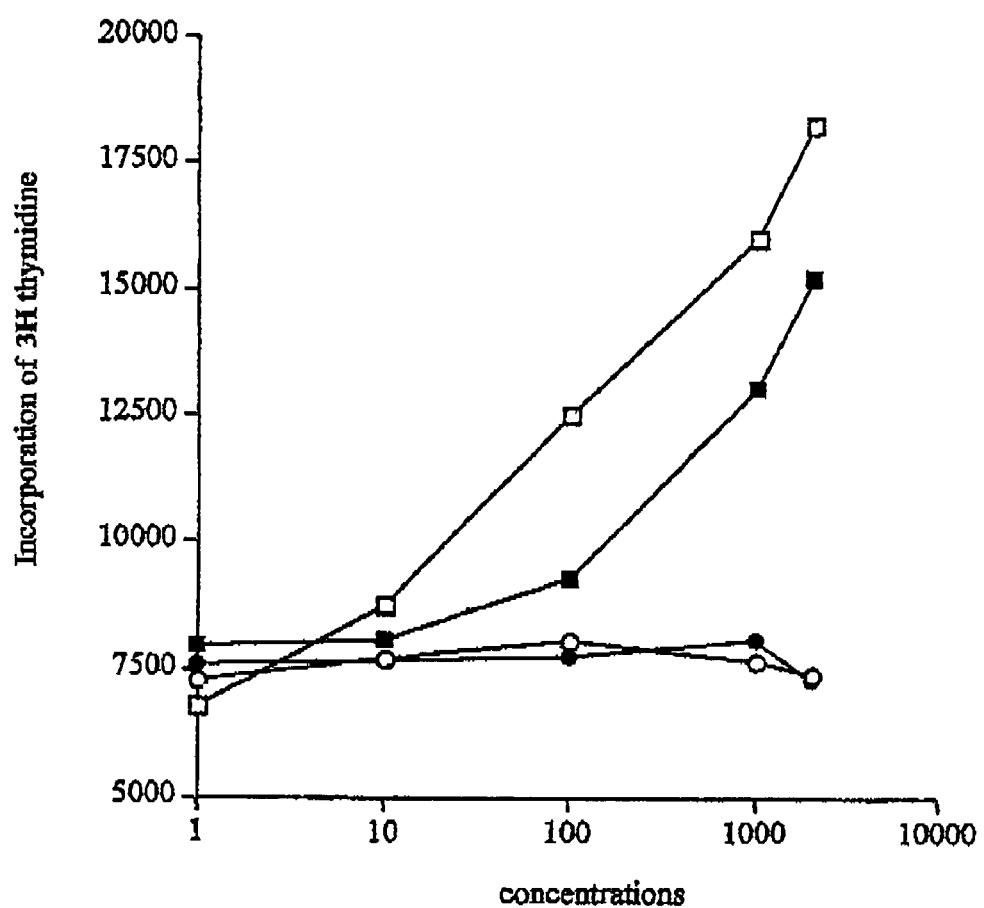

This increase effect of protein ESM-1 on HGF/SF activity was dependent on the dose of ESM-1 and began to be significant at a dose of 10 ng/ml (FIG. 6).

In addition, the effect of protein ESM/WT was compared to the effect of decorin, another proteoglycan of the type chondroitin sulfate/dermatan sulfate, on the mitogenic activity of factor HGF/SF. In contrast to protein ESM/WT, decorin showed no activity of increasing the proliferation of 293 cells induced by factor HGF/SF (FIGS. 5, 6).

These results showed that protein ESM-1 had a specific effect on the mitogenic activity of factor HGF/SF.

In order to examine the respective involvement of the protein part of ESM-1 and of the GAG chain on the activity of increasing the mitogenic effect, the incorporation of $^3$H-thymidine by 293 cells in the presence of HGF/SF supplemented with different concentrations of non-glycosylated ESM/S137A and of the GAG chain derived from of ESM-1 was measured.

The non-glycosylated form of ESM-1 was incapable of inducing a proliferation of the 293 cells, either in the presence or absence of factor HGFSF (FIG. 5), even when it was used at high concentration.

In contrast, the GAG chain purified from ESM-1 considerably increased the proliferation of 293 cells induced by factor HGF/SF, with a factor of increase close to 96.6%, compared to factor HGF/SF alone (FIG. 5). The pro-mitogenic effect of the GAG chain was less than that observed with the wild form of protein ESM-1, but this effect was nevertheless dependent on the dose of GAG chain added (FIG. 6).

The results given above clearly show that protein ESM/WT increases the proliferation of 293 cells induced by factor HGF/SF and that this pro-mitogenic activity is specific and due to the GAG chain of the chondroitin sulfate/dermatan sulfate type of ESM-1.

In general, factor HGF/SF is expressed during the critical early periods of human organogenesis from 6 to 13 weeks of gestation. The organs which express the HGF/SF gene are particularly the liver, metanephric kidney, intestine and lung, each of these organs developing by inductive interaction between the mesenchyma and the epithelium. In addition, factor HGF/SF is an important factor in human renal multcystic dysplasia (TAKAYAMA et al., 1997) and in the appearance of malformation and hyperproliferation in the tubules. The results presented above show that protein ESM-1 significantly increases the proliferation of the cells of the embryonic kidney in the presence of HGF/SF while the nonglycosylated form of protein ESM-1 has no effect. In addition, the GAG chain isolated from protein ESM-1 is able to mimic the effects of the glycosylated protein ESM/WT. These results clearly show that the biological activity of ESM-1 on the function of factor HGF/SF is principally mediated by its GAG chain. It may be noted that decorin, another proteoglycan of the chondroitin sulfate/dermatan sulfate type secreted by endothelial cells and which is able to fix onto factor HGF/SF (CELLA et al., 1992) has no effect on the activity of HGFSF. These comparisons show a specificity of action of protein ESM-1 on the activity of factor HGF/SF requiring a composition of the GAG chain different from the GAG chain of the proteoglycans belonging to the family of proteoglycans with small leucine-rich repeats.

In the kidney, protein ESM-1 is selectively detected in the distal tubules, a result which may be associated with the observation of a preferential localization of factor HGF/SF in the same part of the nephron in situations of human renal multicystic dysplasia (WEIDNER et al., 1993). These results indicate an application of protein ESM-1 in pathological disorders depending on factor HGF/SF, which has also been shown as being associated with the development of cancers of the breast (RAHIMI et al., 1998), kidney (NATALI and al, (1996)) and lung (OTSUKA et al., 1998) and also in malignant melanomas (SIEGFRIED et al., 1998). Thus, factor HGF/SF is likely to favorize the extension of hyperplasia and to generate cells with an invasive phenotype. Protein ESM-1 is likely to be involved in these phenomena of deregulated mitogenic activities of factor HGF/SF.

Example 3

Preparation of an Antagonist Compound of Protein ESM-1 of the Antibody Type

In order to obtain anti-ESM-1 monoclonal antibodies directed against the N-terminal region of protein ESM-1 rich in cysteine residues, the native form of protein ESM-1 produced by the CHO cell line transfected by an expression vector containing a DNA insert coding for protein ESM-1 was purified.

The cDNA of ESM-1 was inserted into the eukaryotic expression vector pcDNA3 (In vitrogen) then transfected in CHO cells with lipofectamine (GIBGO) according to the manufacturer's recommendation. 48 Hours after the transfection the cells were transplanted in the presence of a selection agent (G418, Gibco) at a dose of 1000 microgram/ml). After two weeks of selection, the CHO cells resistant to G418 were cloned by limiting dilution. The clones expressing ESM-1 were then selected and named CHO-ESM (deposited at the CNCM).

For the production, the CHO-ESM cells were cultured in suspension in a medium without foetal calf serum (medium CHO SFM II, Gibco). The supernatant was adjusted to pH 8 and passed over a DEAE-sepharose column (Pharmacia). The column was washed with a buffer 50 mM Tris, pH 8, 0.2 M NaCl. The ESM-1 molecule was eluted in a buffer 50 mM Tris, pH 8, 1 M NaCl. The eluate was then diluted 1:4 in a buffer 50 mM Tris, pH 8 and incubated in the presence of anti-ESM-1 monoclonal antibody (MEC4) immobilized on agarose (Biorad). After incubation overnight at 4° C. with agitation the agarose beads were washed with buffer 50 mM Tris, pH 8, 0.2 M NaCl. ESM-1 was eluted with 3 M MgCl$_2$. The eluate was concentrated and dialysed in buffer 50 mM Tris, pH 8, 0.5 M NaCl and stored at −70° C.

Balb/C mice were immunized by injection of 10 µm of purified recombinant protein ESM-1 per mouse, according to a standard immunization protocol in the presence of Freund's adjuvant.

The hybridoma cells secreting the anti-ESM-1 monoclonal antibodies were obtained by fusion, screening and sub-cloning according to the technique described by BECHARD et al. (2000).

Five hybridoma cell clones were obtained and generically designated MEC (Mouse Monoclonal Antibody to ESM-1 produced by CHO Cells).

Four of the hybridomas selected were of isotypes IgG1, k, respectively the hybridomas designated MEC4, MEC5, MEC15 and MEC36.

One of the hybridomas was of isotype IgM,k, the hybridoma MEC11.

The hybrdoma cell clones were cultured in culture medium in the absence of serum and the anti-ESM-1 antibodies were purified by chromatography on a column of protein G-Sepharose marketed by Pharmacia (UPPSALA, Sweden).

Example 4

Preparation of an Antagonist Compound of Protein ESM-1 of the Polypeptide Type

The directed mutagenesis was performed with the kit marketed by STRATAGENE under the reference Site-directed quick mutagenesis kit, used according to the recommendations of the manufacturer.

Briefly, a pair of forward and reverse primers of strictly complementary sequences were synthesized, these primers comprising the nucleotides coding for the mutated amino acid(s), or the complementary nucleotides, these nucleotides being localized in the centre of the sequence of the primers which also comprise about 10 to 15 consecutive nucleotides complementary to the sequence to be amplified both on the 5' and the 3' side of the central nucleotides.

After amplification by PCR, the amplified polynucleotides coding for the mutant protein ESM-1 were inserted into the vector pcDNA3.

The following pairs of primers respectively were used:

a) For protein ESM-1 F115A

```
Forward primer:  5'-GCC TGA AAT TCC CCG CCT TCC AAT ATT CAG-3'.   (SEQ ID N° 3)
Reverse primer:  5'-CTG AAT ATT GGA AGG CGG GGA ATT TCA GGC-3'.   (SEQ ID N° 4)
``` b) For protein ESM-1 F116A

```
Forward primer:  5'-CCT GAA ATT CCC CTT CGC CCA ATA TTC AGT AAC C-3'.   (SEQ ID N° 5)
Reverse primer:  5'-GGT TAC TGA ATA TTG CGC GAA GGG GAA TTT CAGT G-3'.

(SEQ ID N° 6)
``` c) For protein ESM-1 F115 F116A

```
Forward primer:  5'- CCT GAA ATT CCC CGC CGC CCA ATA TTC AGT AAC C-3'.   (SEQ ID N° 7)
Reverse primer:  5'- GGT TAC TGA ATA TTG GGC GGC GGG GAA TTT CAG G-3'-.  (SEQ ID N° 8)
```

Example 5

Pro-tumorigenic Activity of Glycosylated Protein ESM-1.

A. Materials and Methods

A.1. Cell lines : HEK T. HEK ESM/WT, HEK ESM/S137A, HEK ESM/69, HEK ESM/71, HEK ESM/73.

The cell line HEK ESM/WT transfected stably with the cDNA coding for the wild form of ESM-1 (ESM/WT) was used. Four other cell lines were obtained by transfection with the cDNA coding for the purified forms of ESM-1 obtained by directed mutagenesis of the wild type. The first of these, named HEK ESM/S137A, expressed the mutant non-glycosylated protein ESM-1, where an alanine has replaced serine 137, the major site of O-glycosylation. The three other lines expressed a glycosylated form of ESM-1 whose protein part has been mutated. They were lines HEK ESM/F115A (replacement of the phenylalanine in position 134, HEK ESM/71 (replacement of the phenylalanine in position 135) and HEK ESM/F115A, F116A (double deletion/replacement 134-135).

Thus, six cell line producing different forms of ESM-1 were used:
control HEK, not secreting ESM-1;
Wild form of ESM-1: HEK ESM/WT;
Deglycosylated form of ESM-1: HEK ESM/S137A;
Glycosylated forms whose protein part has been mutated in the region 115-116; HEK-ESM/69, HEK-ESM/71, HEK ESM/73.

A2. Murine Model of Xenogenic Tumours

The mice used were of type SCID (Severe Combined IMMUNO Deficiency). They were more precisely mice C.B.17 Scid/scid supplied by the animal service of the Institut Pasteur of Lille. These mice had a recessive autosomal mutation in their recombination system (Blunt., 1995). This mutation causes the production of non-functional immunoglobulins and T cell receptors (TcR) and B 5BcR) As a result, they do not possess functional T and B lymphocytes; these mice therefore tolerate non-self and represent a model of choice for the development of xenogenic tumours. The SCID mice used were young male mice aged from 3 to 5 weeks. For each of them, an intra-peritoneal injection of anti-ascialo GM-1 antibodies (100 μg per mouse diluted in 200 μl of RPMI) was performed 24 hours before injection with the different cell lines. These were rabbit polyclonal antibodies (Wako Pure Chemical Industries, Ltd) directed specifically against the asialo GM-1 antigen expressed by NK cells. Previous work has shown that the use of these antibodies in mudne models neutralizes the cytotoxic effect of the NK cells and encourages the tumoral grafting (Mather G et al. (1994).

Four batches of mice (10 to 15 mice per group) anaesthetized with ether, were then injected subcutaneously in the back. Each mouse received 1 million cells diluted in 200 μl of RPMI. The injection of these cells defined the first day of the experiment (D0). For each mouse, macroscopic inspection of the point of injection in order to observe the appearance of a possible tumour, as well as measurement of body weight, was performed weekly. A blood sample (about 500 µl per mouse) was weekly taken from the 5th week onwards, in order to determine the serum levels of ESM-1 by an ELISA test (BECHARD D) et al., 2000). An anatomopathological examination was performed on each mouse.

B. Results

B.1. Induction of Tumours in Mice by Glycosylated Protein ESM-1.

HEK cells were transfected with a vector possessing an insert containing the cDNA coding for glycosylated wild protein ESM-1, designated ESM/WT. The HEK cells were injected subcutaneously into SCID mice aged 5 weeks. Each mouse had previously received an intraperitoneal injection of anti-asialo GN-1 antibodies.

The percentage of tumours having a volume greater than 1 cm$^3$ observed in the mice at the eighth week following the injection of the transfected HEK cells was analysed.

The results are given on FIG. 7.

Figure 7A:
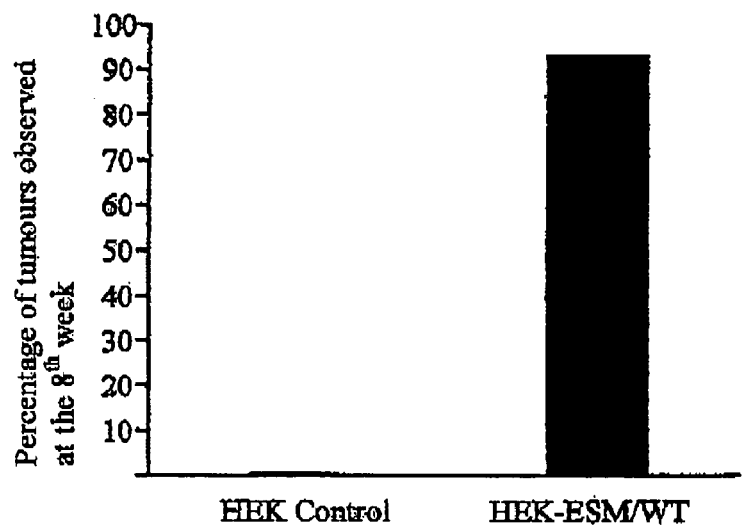

On FIG. 7A, it can be observed that the injection of control HEK cells did not induce the appearance of tumours in mice In contrast, the HEK cells transfected with a DNA coding for glycosylated protein ESM-1 induced numerous macroscopically visible tumours, of which about 95% had a tumoral volume greater than 1 cm$^3$.

Figure 7B:
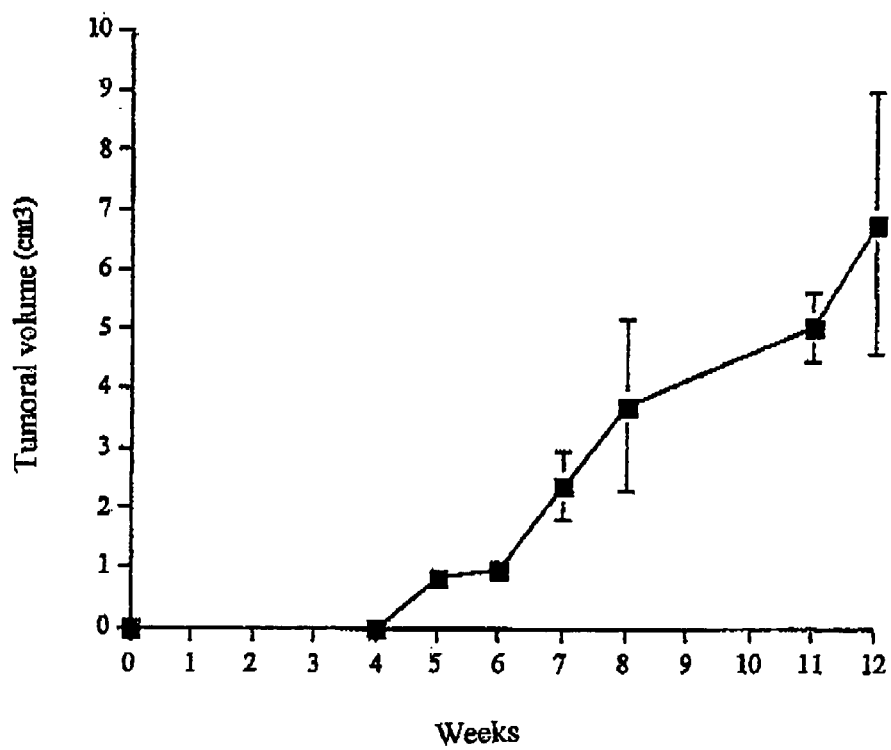

FIG. 7B illustrates the kinetics of appearance of tumours in mice which had received transfected HEK cells transfected with a DNA coding for glycosylated protein ESM-1. It can be observed that the mean tumoral volume, expressed in cm$^3$, increased continuously from the fourth week following the injection of the transfected HEK cells.

The experimental results presented in FIG. 7 clearly show that glycosylated protein ESM-1 has a pro-tumoral activity.

The serum levels of protein ESM-1 were also measured in mice having received control HEK cells and mice having received HEK cells transfected with cDNA coding for protein ESM-1.

The results are shown on FIG. 8.

Figure 8A:
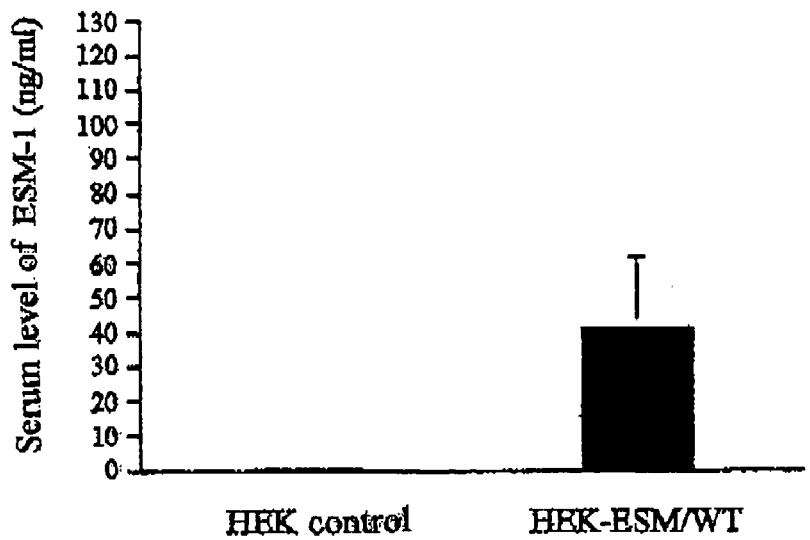
FIG. 8B illustrates the kinetics of the serum levels of ESM-1 measured by ELISA, for the mice of the batch having received the HEK cells transfected with a DNA coding for the glycosylated protein ESM-1 (ESM/WT). The abscissa shows the number of weeks following the injection of the transfected cells The serum level of protein ESM-1, expressed in nanogram/ml, is given on the ordinate.

The results illustrated in FIG. 8A show that protein ESM-1 was not found in the serums of mice having received control HEK cells. In contrast, a serum level of 40 to 50 nanograms per ml was found in mice having received HEK cells transfected with cDNA coding for protein ESM-1 at the eighth week following injection of the cells.

The kinetics of the serum levels of ESM-1 in mice having received transfected HEK cells expressing glycosylated protein ESM-1 (ESM/IT) were also analysed.

Figure 8B:
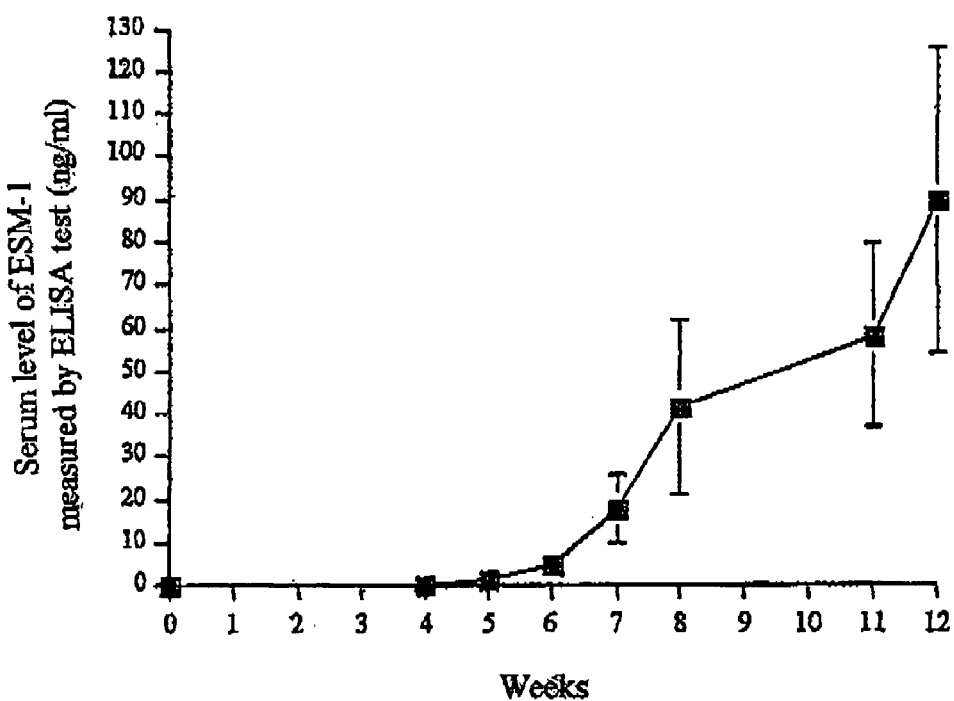

The results are given in FIG. 8B.

It can be observed that a detectable quantity of protein ESM-1 was found in the serum of mice from the fifth week following the injection of cells and that the serum level increased rapidly and continuously from the fifth to the twelfth week following injection of the cells.

The experimental results illustrated in FIG. 8 show that the tumours which developed in mice having received transfected HEK cells produce protein ESM-1. In addition, the quantity of protein ESM-1 produced in the circulation follows the kinetics of development of the tumours in the mice.

Example 6

Pro-tumorigenic Activity of Different Forms of Protein ESM-1

A. Materials and Methods

The materials and methods used in this example are identical to those described for example 5.

B. Results

The HEK cells were transfected by vectors possessing a DNA insert coding respectively for the nonglycosylated wild form of ESM-1 (ESM/WT), a non-glycosylated form of ESM-1 (ESM/S137A) and a glycosylated form of ESM-1 mutated at the phenylalanine residues in positions 134 and 135 which have both been replaced by an alanine residue (ESM/73). The different transfected cells were injected subcutaneously into SCID mice aged 5 weeks and having previously received anti-asialo GM-1 antibodies.

The percentage of tumours macroscopically visible having a tumoral volume greater than 1 am$^3$ in the different batches of mice was analysed. The results are shown on FIG. 9A.

The results of FIG. 9A show that only the glycosytated protein ESM-1 is able to induce tumours in mice. Neither the non-glycosylated ESM-1 nor the glycosylated ESM-1 mutated at the phenylalanine residues in positions 134 and 135 induced the development of tumours in SCID mice.

The serum levels of protein ESM-1 circulating in the different batches of mice were also measured. The results are given in FIG. 9B.

The results on FIG. 9B show that detectable levels of serum protein ESM-1 could be measured, at the eighth week following injection of the cells, only in the mice having received the HEK cells expressing glycosylated protein ESM-1 (ESM/WT).

Neither the mice injected with cells expressing the non-glycosylated protein ESM-1 (ESM/S137A), nor the mice having received the glycosylated and mutated protein ESM-1 HEK-ESM/F115A, F116A) produced protein ESM-1.

The overall results presented in this example confirm the pro-tumorigenic activity of glycosylated protein ESM-1.

The results also show that the non-glycosylated forms of protein ESM-1 or the mutant forms of protein ESM-1 can behave as antagonists of this protein and possess preventive and/or curative power with regard to cancerous pathologies.

Example 7

Determination of Circulating Protein ESM-1 in Patients Suffering from Broncho-pulmonary Cancers at Different Stages of Development A. Materials and Method The immunodetection test consisted of an immuno-enzymatic test of the "sandwich" type whose general characteristics are identical to those described by BECHARD et al. (2000).

The anti-ESM-1 monoclonal antibody produced by the hybridoma lines MEP14 (CNCM N°I-1942) was diluted to a concentration of 5 µg/ml in a carbonate buffer 0.1 M, pH 95, and adsorbed overnight at +4° C. on a 96-well plate (plate E.I.A./R.I.A., Costar, Cambridge, Mass., USA).

The plate was saturated for one hour at laboratory temperature with a volume of 200 µl/well of PBS buffer containing 0.1% of bovine serum albumin and 5 mM of EDTA, then washed twice with an ELISA buffer (the PBS buffer above supplemented with 0.1% Tween 20).

A calibration was performed with protein ESM-1 purified according to the technique described by BECHARD et al. (2000).

The blood samples were serially diluted (1:2 to 1:128), in an ELISA buffer and incubated on an ELISA plate for one hour at laboratory temperature.

The wells were washed three times with an ELISA buffer, then incubated for 1 hour at laboratory temperature with a second monoclonal antibody directed against ESM-1, the antibody MEC15 (CNCM N°I-2572) at a concentration of 0.1 μg/ml in 100 μl of buffer per well.

After three washings, a biotinylated rat monoclonal antibody rat directed against mouse IgG1 (marketed by PHARMINGEN) diluted in an ELISA buffer was added and left to incubate this second antibody for one hour.

After three washings in the ELISA buffer, the wells were incubated with a streptavidine-peroxidase conjugate at a dilution 1:10.000 v/v (marketed by ZYMED).

After 30 minutes of incubation-with the streptavidine-peroxidase conjugate, three washings of each well were performed with an ELISA buffer, then two washings in a PBS buffer.

The streptavidine-peroxidase conjugate was revealed with the substrate TMB marketed by SIGMA (Saint-Louis, Mo., USA) in the presence of 255 μl of $H_2O_2$ for 30'.

The revelation reaction was stopped by addition of a volume of 100 μl of $H_2SO_4$ 2N.

The plate was read using a spectrophotometer (anthos labtec LP40. France) at a wavelength of 405 nanometres.

The plasma or serum concentration of protein ESM-1 was calculated from the optical density measurements and expressed in nanograms per ml.

B. Results

The concentration of protein ESM-1 circulating in the serum of different patients -with broncho-pulmonary cancer at different stages development, respectively at stage I, II, IIIA, IIIB and IV according to the international classification TNM defined below:

T=size of the tumour (T1:<1 cm; T2: between 1 and 3 cm; T3:>3 cm.

N=ganglion nodule (NO if not invaded; N1 if invaded).

M=metastasis at distance (MO if no metastasis; M if metastasis).

The patients suffering from cancer at stage I had a serum concentration of protein ESM-1 of 1.43+/−0.76 nanograms/ml (n=3).

The patients suffering from a bronchopulmonary cancer at stage If had a serum concentration of protein ESM-1 of 0.72+/−0.39 nanograms/ml (n=3).

The patients suffering from a bronchopulmonary cancer at stage IIIA had a concentration of circulating protein ESM-1 of 0.9+/−0.53 nanograms/ml (n=2).

The patients suffering from a bronchopulmonary cancer at stage IIIB had a concentration of circulating protein ESM-1 of 3.1+/−2.17 nanograms/ml (n=3).

The patients suffering from a bronchopulmonary cancer at stage IV had a concentration of circulating protein ESM-1 of 3.1+/−1.91 nanograms/ml (n=11).

The results given above show that the serum levels of protein ESM-1 increase as a function of the stage of development of the cancer. A clear relation is thus demonstrated between the level of production of protein ESM-1 in the blood circulation and the severity of a cancer in a patient.

Example 8

Anti-tumoral Activity of an Antagonist Compound of ESM-1 of the Antibody Type

A. Materials and Method

MEP08 monoclonal antibodies were injected intraperitoneally at a dose of 400 μg from the second following the inoculation of HEK/ESM-WT cells. The injections were repeated weekly for 12 weeks. A control antibody, MEP-14, was used under the same conditions. The mice were sacrificed when their tumoral volume was greater than 6 $cm^3$. (n>8 mice in each group). The figure shows the percentage of surviving mice in each of the groups.

B. Results

To the extent that the phenylalanine in position 115 is necessary for tumoral development, it comprises a new therapeutic target. For this reason the anti-ESM-1 monoclonal antibodies MEP-08, produced by the hybridoma line MEP-08 deposited at the CNCM under the n°I-1941, directed specifically against this region, were produced and injected into the group of HEK-ESM/WT mice. The object was to study the role of the peptide of ESM-1 in the tumoral development and to evaluate a possible therapeutic effect. In order to eliminate an anti-tumoral effect depending on the fragment Fc of the antibody (reaction of ADCC), a control antibody of the same isotype but recognizing a different epitope was used in parallel and under the same conditions.

FIG. 10 shows that the early injections of MEP-08 antibodies significantly increased the survival of the mice by nearly 60% while the MEP-14 antibodies had no effect. These first results show that this is a specific action linked to the fragment Fab of the antibody directed specifically against the phenylalanine in position 115 and confirm the involvement of the peptide in the tumoral growth. It is surprising to observe that this effect on the survival reduces when the antibodies are administered later.

Whichever week the injections begin, the antibodies can delay or prevent the tumoral growth. This anti-tumoral effect remains more pronounced when the antibodies are used earlier.

BIBLIOGRAPHIC REFERENCES

ANFOSSI et al. (1989), Acad. Sci., vol.86:3379-3383
AUSUBEL F. et al. K, 1989, Current Protocols in Molecular Biology
GREEN publishing Associates and WILEY lnterscience, N.Y.
BECHARD et al. 2000. J. Vasc, Res. 37(5): 417-425.
BEAUCAGE et al., 1981, Tetrahedron Lett., vol.22: 1859-1862
BLUNT (1995) [Référence á compléter S.V.P.].
BROWN E L, BELAGAJE R, RYAN M J, KHORANA H G, Methods
ENZYMOL, 1979, Vol. 68: 109-151
BUSH et al., 1997, J. Chromatogr. , vol.777: 311-328
CELLA G et al., 1992, Angiology, vol.43
DELORME M A et al., (1996, Thromb Haemost, vol.75: 747-751.)
EDWARDS and LEATHERBARROW, 1997, Analytical Biochemistry, vol. 246: 1-6.
FELICI F, 1991, J. Mol. Biol., vol. 222:301-310
GAO and al, 1996, J. Biol. Chem, vol. 271 (15):9002-9008
GLUZMAN , 1982, Eukaryotic Viral Vectors, Cold Spring Harbor Laboratory.

GREEN et al., 1986, Ann. Rev. Biochem., vol.55: 569-597
HOLT and al, 1988, Mol. Cell. Biol. vol.8 : 963-973
HOUBEN WEYL, 1974, in Meuthode der Organischen Chemie,
E. WUNSCH ed, vols. 15-1 and 15-2
IZANT J G, WEINTRAUB H, 1984, Cell, vol.36 (4): 1007-1015
KOHLER G. and MIELSTEIN C., 1975, Nat. Vol.256:495.
KOZBOR et al. (1983), Hybridoma, vol.2 (1): 7-16
LASSALLE P et al., 1996, The Journal of Biological Chemistry, vol.271(34): 20.458-20.464.
LASSALLE P et al., 1992, Eur. J. Immunol., vol.22:425-431
LEGER et al. (1-997), Hum. antibodies, vol.8 (1): 3-16.
LUCAS A H, 1994, In: Development and Clinical uses of haemophilus b Conjuguate
MATHER G et al. 1994, Immunobiology, 190 (4-5): 333-345.
MARTINEAU P, JONES P., WINTER G et al., 1998, J. Mol. Biol, vol.280(1): 117-127.
MERRIFIELD R B, 1965a, Nat, vol.207(996): 522-523
MERRIFIELD R B 1965b Science, vol.150(693;178-185)
MOXHAM et al., 1993, Science, vol.2602: 991-995.
NARANG S A, HSIUNG H N, BROUSSEAU R. et al. 1979, Methods enzymol, vol.68 ,90-98
NATALI P G et al., 1996, Int. J. Cancer, vol.69:212-217
LEE and NATHANS, 1988, J. Biol. Chem., vol.263: 3521
OLDENBURG K R et al., 1992, Proc Natl. Acad. Sci, vol. 89: 5393-5397
RAHIMI N et al. (1998), J. Biol. Chem., vol.273:33.714-33.721
RIDDER R, SCHMITZ R, LEGAY F. GRAM H. 1995, Biotechnology (N.Y.), vol.13 (3): 255-260.
SIEGFRIED J M et al., 1998, Ann. Thorac. Surg., vol.66: 1915-1918
OTSUKA T et al., 1998, Cancer Res., vol.58:5157-5167
PARMLEY and SMITH, 1988, Gene, vol.73: 305-318
REINMANN K A et al., 1997, AIDS Res. Hum. Retroviruses, vol.13 (11):933-943
ROSSI et al., 1991, Pharmacol. Ther, vol.50 : 245-254
SALE and al, 1995, EMBO J. vol.14 (4): 674-684
SCZAKIEL G et al., 1995, Trends Microbiol, vol.3 (6); 213-217
TAKAYAMA H and al, 1997, Lab. Invest vol.77: 131-138
VALADON P et al.,1996, J. Mol. Biol., vol. 261: 11-22
WANG et al., 1997, Chromatographia, vol.44: 205-208
WESTERING M A J, 1995, Proc. Natl. acad. sci, vol.92: 4021-4025
WICKSTROM and al, 1988, Proc. Natl. acad. sci. vol.85: 1028-1032
WEIDNER K M et al., 1993, J. Cell Biol. vol. 121: 141-154

The invention claimed is:

1. A method of inhibiting or blocking the tumorigenic capacity of ESM-1 protein in a cancer patient, wherein said method comprises administering to the patient a pharmaceutical composition comprising (i) a monoclonal antibody produced by the hybridoma line deposited at the Collection National de Cultures de Microorganismes of the Institut Pasteur under accession No. I-1941, also named MEP08, in an amount that inhibits or blocks the tumorigenic capacity of ESM-1 protein in vivo, and (ii) one or more pharmaceutically acceptable vehicles.

* * * * *

UNITED STATES PATENT AND TRADEMARK OFFICE
CERTIFICATE OF CORRECTION

PATENT NO. : 7,306,797 B2 Page 1 of 1
APPLICATION NO. : 10/416203
DATED : December 11, 2007
INVENTOR(S) : Lassalle et al.

It is certified that error appears in the above-identified patent and that said Letters Patent is hereby corrected as shown below:

On the title page, item (86), line 3, "Apr. 26, 2004" should read --May 8, 2003--.

Signed and Sealed this

Third Day of June, 2008

JON W. DUDAS
*Director of the United States Patent and Trademark Office*